(12) United States Patent
Suddaby

(10) Patent No.: US 9,968,379 B2
(45) Date of Patent: May 15, 2018

(54) SUBCUTANEOUS IMPLANTABLE DEVICE FOR GRADUALLY ALIGNING A SPINE AND SUBCUTANEOUS IMPLANTABLE DEVICE FOR GRADUALLY LENGTHENING A BONE

(71) Applicant: Loubert S. Suddaby, Orchard Park, NY (US)

(72) Inventor: Loubert S. Suddaby, Orchard Park, NY (US)

( * ) Notice: Subject to any disclaimer, the term of this patent is extended or adjusted under 35 U.S.C. 154(b) by 141 days.

(21) Appl. No.: 14/995,382

(22) Filed: Jan. 14, 2016

(65) Prior Publication Data

US 2016/0128735 A1 May 12, 2016

Related U.S. Application Data

(63) Continuation-in-part of application No. 14/244,241, filed on Apr. 3, 2014, now Pat. No. 9,480,519, which
(Continued)

(51) Int. Cl.
*A61B 17/70* (2006.01)
*A61B 17/66* (2006.01)
(Continued)

(52) U.S. Cl.
CPC .......... *A61B 17/7053* (2013.01); *A61B 17/66* (2013.01); *A61B 17/683* (2013.01); *A61B 17/686* (2013.01); *A61B 17/7059* (2013.01); *A61B 17/7216* (2013.01); *A61B 17/8685* (2013.01); *A61B 17/8855* (2013.01); *A61B 17/8869* (2013.01); *A61B 2017/00004* (2013.01); *A61B 2017/565* (2013.01)

(58) Field of Classification Search
CPC .......................... A61B 17/7053; A61B 17/8869
See application file for complete search history.

(56) References Cited

U.S. PATENT DOCUMENTS

| 1,949,969 A | 3/1932 | Longfellow |
| 2,867,819 A | 1/1959 | George |

(Continued)

OTHER PUBLICATIONS

Cundy, Peter J.; Paterson, Dennis C.; Hillier, Terence M.; Sutherland, Andrew D.; Stephen, John P.; Foster, Bruce K., Cotrel-Dubousset Instrumentation and Vertebral Rotation in Adolescent Idiopathic Scoliosis. The Journal of Bone and Joint Surgery, 1990, pp. 670-674, J Bone Joint Surg, British Editorial Society of Bone and Joint Surgery.

*Primary Examiner* — Ellen C Hammond
(74) *Attorney, Agent, or Firm* — Simpson & Simpson, PLLC

(57) ABSTRACT

A subcutaneous implantable device for aligning a spine having a plurality of vertebrae including a first brace assembly secured to a first vertebra of the spine, a second brace assembly secured to a second vertebra of the spine, a rod secured by the at least two brace assemblies, the rod arranged for limited sliding movement within the at least two brace assemblies, a gear mechanism attached to the rod, a control means attached to the gear mechanism, and a cable fixedly secured to a third vertebra of the spine by an anchor. The third vertebra is located between the first and second vertebrae, and the cable is arranged for pulling the third vertebra towards the rod. A subcutaneous implantable device for gradually lengthening a bone.

22 Claims, 38 Drawing Sheets

Related U.S. Application Data is a continuation-in-part of application No. 13/644,365, filed on Oct. 4, 2012, now Pat. No. 8,764,803.

(51) Int. Cl.
| | | |
|---|---|---|
| *A61B 17/68* | (2006.01) | |
| *A61B 17/86* | (2006.01) | |
| *A61B 17/88* | (2006.01) | |
| *A61B 17/72* | (2006.01) | |
| *A61B 17/00* | (2006.01) | |
| *A61B 17/56* | (2006.01) | |

(56) References Cited

U.S. PATENT DOCUMENTS

| | | | |
|---|---|---|---|
| 3,809,074 A | 5/1974 | De Moude | |
| 4,047,523 A | 9/1977 | Hall | |
| 4,262,665 A | 4/1981 | Roalstad et al. | |
| 4,273,116 A | 6/1981 | Chiquet | |
| 5,122,140 A | 6/1992 | Asche et al. | |
| 5,782,831 A * | 7/1998 | Sherman | A61B 17/7041 |
| | | | 606/103 |
| 5,863,292 A | 1/1999 | Tosic | |
| 5,893,850 A | 4/1999 | Cachia | |
| 5,928,230 A | 7/1999 | Tosic | |
| 6,033,429 A | 3/2000 | Magovern | |
| 6,077,268 A | 6/2000 | Farris et al. | |
| 6,086,590 A | 7/2000 | Margulies et al. | |
| 6,146,386 A | 11/2000 | Blackman et al. | |
| 6,290,700 B1 | 9/2001 | Schmotzer | |
| 6,423,065 B2 | 7/2002 | Ferree | |
| 6,551,320 B2 | 4/2003 | Lieberman | |
| 6,648,890 B2 | 11/2003 | Culbert et al. | |
| 6,676,665 B2 | 1/2004 | Foley et al. | |
| 7,632,277 B2 | 12/2009 | Woll et al. | |
| 7,842,072 B2 | 11/2010 | Dawson | |
| 8,083,741 B2 | 12/2011 | Morgan et al. | |
| 8,114,158 B2 | 2/2012 | Carl et al. | |
| 8,162,979 B2 | 4/2012 | Sachs et al. | |
| 8,267,971 B2 | 9/2012 | Dutoit et al. | |
| 8,323,294 B2 | 12/2012 | Mickiewicz et al. | |
| 8,357,182 B2 | 1/2013 | Seme | |
| 8,357,183 B2 | 1/2013 | Seme et al. | |
| 8,512,343 B2 | 8/2013 | Dziedzic et al. | |
| 8,672,944 B2 | 3/2014 | Boachie-Adjei et al. | |
| 8,764,803 B2 | 7/2014 | Suddaby | |
| 8,828,058 B2 | 9/2014 | Elsebaie et al. | |
| 8,920,472 B2 | 12/2014 | Seme et al. | |
| 9,333,009 B2 * | 5/2016 | Kroll | A61B 17/7014 |
| 2002/0082600 A1 * | 6/2002 | Shaolian | A61B 17/1671 |
| | | | 606/262 |
| 2003/0120301 A1 | 6/2003 | Yock | |
| 2003/0158557 A1 | 8/2003 | Cragg et al. | |
| 2004/0049202 A1 | 3/2004 | Berger | |
| 2004/0097944 A1 | 5/2004 | Koman et al. | |
| 2006/0047282 A1 | 3/2006 | Gordon | |
| 2006/0195090 A1 | 8/2006 | Suddaby | |
| 2006/0217736 A1 | 9/2006 | Kaneko et al. | |
| 2007/0016202 A1 | 1/2007 | Kraft et al. | |
| 2007/0270876 A1 | 11/2007 | Kuo et al. | |
| 2008/0023012 A1 | 1/2008 | Dineen et al. | |
| 2008/0051707 A1 | 2/2008 | Phan et al. | |
| 2009/0012565 A1 | 1/2009 | Sachs et al. | |
| 2009/0088799 A1 | 4/2009 | Yeh | |
| 2009/0093820 A1 | 4/2009 | Trieu et al. | |
| 2009/0112262 A1 | 4/2009 | Pool et al. | |
| 2009/0112263 A1 | 4/2009 | Pool et al. | |
| 2009/0281575 A1 | 11/2009 | Carls et al. | |
| 2010/0063545 A1 * | 3/2010 | Richelsoph | A61B 17/7014 |
| | | | 606/264 |
| 2010/0145392 A1 | 6/2010 | Dutoit et al. | |
| 2010/0185241 A1 | 7/2010 | Malandain | |
| 2010/0318129 A1 | 12/2010 | Seme et al. | |
| 2011/0054536 A1 | 3/2011 | Elsebaie et al. | |
| 2011/0066188 A1 | 3/2011 | Seme et al. | |
| 2011/0230806 A1 | 9/2011 | Lou et al. | |
| 2011/0295170 A1 | 12/2011 | Laranjeira Games et al. | |
| 2012/0016369 A1 | 1/2012 | O'Halloran et al. | |
| 2012/0016371 A1 | 1/2012 | O'Halloran et al. | |
| 2012/0059419 A1 | 3/2012 | Alamin et al. | |
| 2012/0059423 A1 | 3/2012 | Young | |
| 2012/0157996 A1 | 6/2012 | Walker et al. | |
| 2012/0203282 A1 | 8/2012 | Sachs et al. | |
| 2013/0211455 A1 | 8/2013 | Seme | |
| 2014/0236234 A1 * | 8/2014 | Kroll | A61B 17/7014 |
| | | | 606/264 |
| 2015/0196342 A1 | 7/2015 | Suddaby | |

* cited by examiner

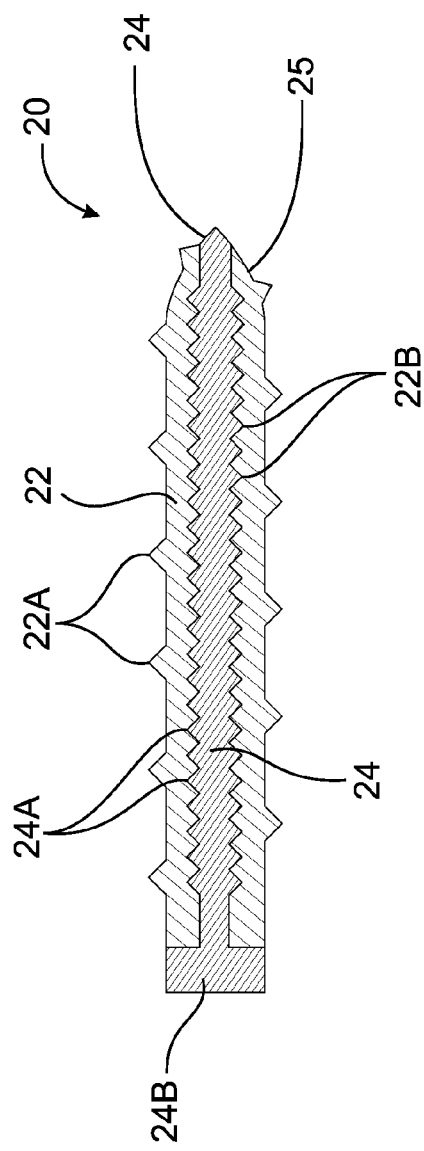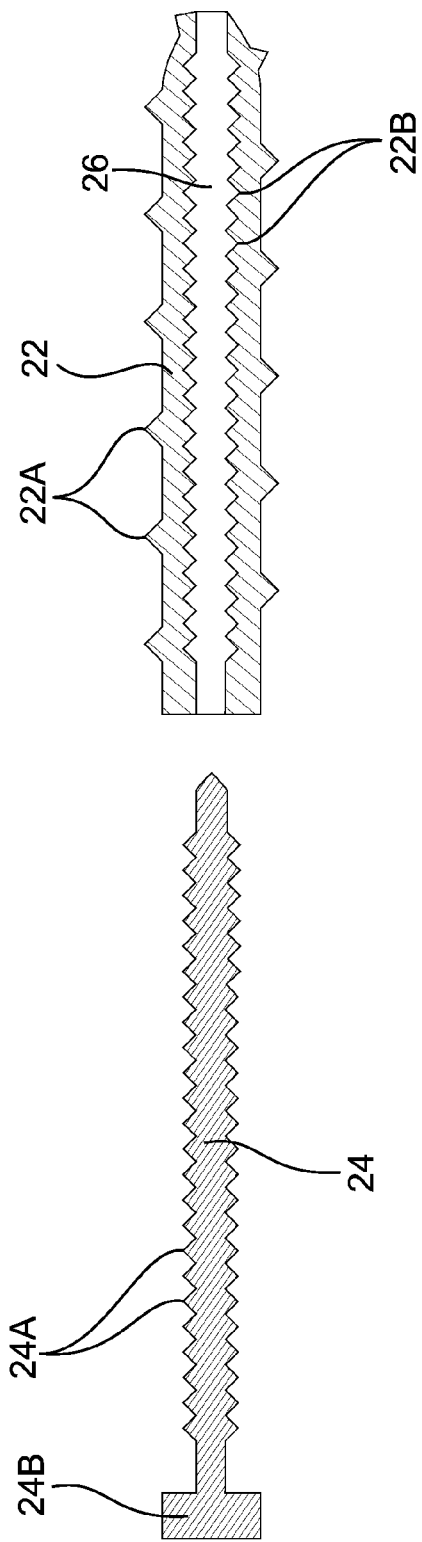
Fig. 3
Fig. 4
Fig. 4A

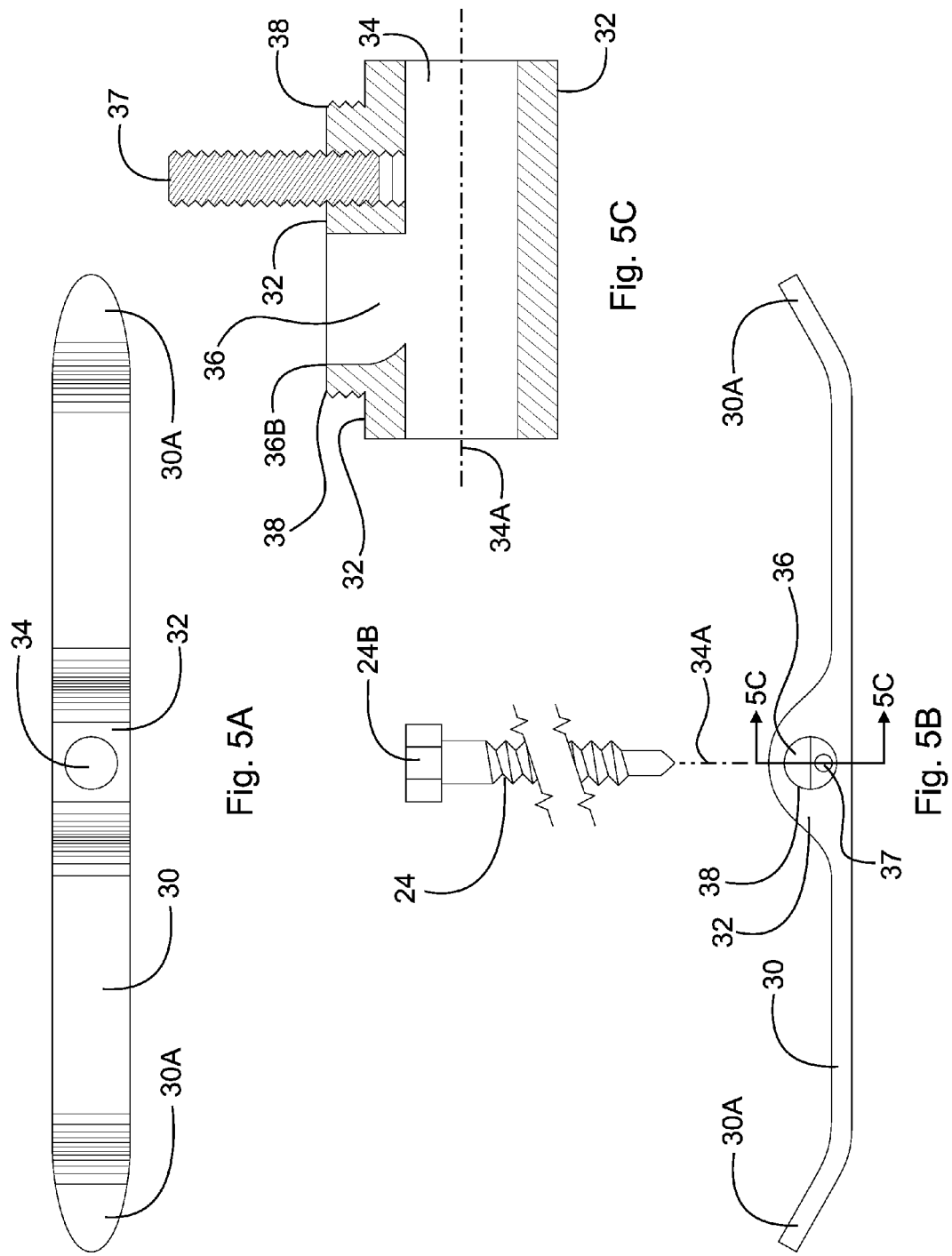

SUBCUTANEOUS IMPLANTABLE DEVICE FOR GRADUALLY ALIGNING A SPINE AND SUBCUTANEOUS IMPLANTABLE DEVICE FOR GRADUALLY LENGTHENING A BONE

CROSS REFERENCE TO RELATED APPLICATIONS

This application is a continuation-in-part patent application filed under 35 U.S.C. § § 111(a) and 120 of U.S. patent application Ser. No. 14/244,241, filed Apr. 3, 2014, which application is a continuation-in-part patent application of U.S. patent application Ser. No. 13/644,365, filed Oct. 4, 2012, now U.S. Pat. No. 8,764,803, issued Jul. 1, 2014, which applications are hereby incorporated by reference in their entireties.

FIELD OF THE INVENTION

The present invention relates to surgical devices, and, more particularly, to orthopedic surgical devices, and, more particularly, to corrective orthopedic surgical devices related to the spine.

BACKGROUND OF THE INVENTION

Scoliosis is a disorder that causes an abnormal curve of the spine, or backbone. Patients with scoliosis develop abnormal curves to either side of the body's median line (lateral curve) and the bones of the spine twist on each other like a corkscrew. Scoliosis is about two times more common in girls than boys. It can be seen at any age, but it is most common in those over 10 years old.

FIG. 1 is a stylized posterior view of a person P with a spine afflicted with scoliosis. Spinal column 1 is shown to have two lateral curves—upper curve 2 and lower curve 3. Often the presence of one lateral curve generates the formation of a second curve to compensate for the reduced spinal support of the body caused by one lateral curve. FIGS. 2A and 2B depict two different types of prior art braces 4 and 5, respectively, used to prevent further deterioration of spinal alignment. In some cases, braces such as braces 4 and 5 may improve the condition, but they rarely enable the wearer to achieve a full recovery to a correct spinal alignment.

Often, the cause of scoliosis is unknown and is described based on the age when scoliosis develops. If the person is less than 3 years old, it is called infantile idiopathic scoliosis. Scoliosis that develops between 3 and 10 years of age is called juvenile idiopathic scoliosis, and people that are over 10 years old have adolescent idiopathic scoliosis.

In functional scoliosis, the spine is normal, but an abnormal curve develops because of a problem somewhere else in the body. This could be caused by one leg being shorter than the other or by muscle spasms in the back. In the neuromuscular form, there is a problem during the formation of the bones of the spine. Either the bones of the spine fail to form completely or they fail to separate from each other. This type of scoliosis may develop in people with other disorders including birth defects, muscular dystrophy, cerebral palsy, and Marfan's disease. This type of scoliosis is often much more severe and needs more aggressive treatment than other forms of scoliosis. Degenerative scoliosis occurs in older adults. It is caused by changes in the spine due to arthritis. Weakening of the normal ligaments and other soft tissues of the spine combined with abnormal bone spurs can lead to an abnormal curvature of the spine.

Adolescent idiopathic scoliosis is the most common form of scoliosis. If the angle of the spinal curve (Cobb's angle) is small when first diagnosed, it can be observed and followed with routine X-rays and measurements. If the curve stays below 25 degrees, no other treatment is usually needed. If the curve is between 25-40 degrees, the curve can be considered significant and a brace may be recommended. If the curve is greater than 40 degrees, the curve can be considered severe and surgery may be recommended. Braces are not designed to correct severe spinal curves. They are used to help slow or stop the curve from getting worse. Since surgery is recommended typically only when the curve is considered significant or severe, surgeons are limited to performing surgical procedures on a subset of the population of individuals diagnosed with scoliosis.

Spinal fusion is one surgical procedure that may be used to alleviate scoliosis. In this procedure, bone is grafted to the vertebrae to form a rigid column. The rigidity of the column prevents the curve from worsening. However, the rigid column reduces the range of motion available to the patient.

Modern surgical procedures attempt to address sagittal imbalance and rotational defects unresolved by the earlier rod systems. They primarily involve a combination of rods, screws, hooks, cables and/or wires fixing the spine and applying forces to the spine to correct the spinal curvature. An example of the use of screws and cables is seen in U.S. Patent Application Publication No. 2006/0195090 (Suddaby) which is hereby incorporated by reference in its entirety. Suddaby discloses a system for improving the alignment of a spine by placing a series of screws or pins into the posterior or lateral side of the bodies of individual vertebrae. Hollow spacers are placed between the pins and a cable is extended through the heads of the pins and the spacers and is attached to an expansion sleeve. Tension is applied to the cable by pulling it through the expansion sleeve and then applying tension to the cable to pull the attached pins into an improved alignment. One of a plurality of nodules at the end of the cable is then placed into the passage of the expansion sleeve thereby holding the cable in the new "tensioned" position. The tension discourages movement of the spine.

U.S. Pat. No. 6,551,320 (Lieberman) discloses an apparatus for aligning a spine that includes a plurality of anchors screwed into adjacent vertebral bodies. A cable or series of cables is strung through or around the anchors and then pulled. The tension applied to the cable(s) is used to pull the spine into a desired alignment. U.S. Patent Application Publication No. 2009/0112262 (Pool et al.) discloses a system in which at least one anchor is screwed or otherwise embedded into an upper vertebra and one or more anchors are similarly placed in lower vertebra(ae). A cable is extended between the anchors and force applied to the cable by a magnetic adjustment device to align the spine. In some cases a second anchor-cable arrangement can be used on the opposite side of the spine.

U.S. Pat. No. 5,782,831 (Sherman et al.) discloses a system for reducing a displaced vertebra between adjacent vertebrae. The Sherman patent describes a system in which two anchors are screwed into the vertebrae on either side of the displaced vertebra with a rod attached between the anchors. A third anchor is screwed into the displaced vertebra and attached to a cable. A cable tightening device, such as a come-along type device is used to pull the displaced vertebra into alignment after which it is attached to the support rod. However, the attachment of a bar across three adjacent vertebrae prevents pulling a curved spine into a more proper alignment.

In attempting to solve spinal alignment and displacement problems, the prior art relies on multiple vertebral anchors and the application of alignment force through complicated force applicators and cable systems. Such corrective systems can be prohibitively expensive. Additionally, typical corrective systems involve the risk of permanent neurological injury caused by stretching the spinal cord. Other typical risks of surgical corrective systems for treating scoliosis involve infection, blood loss, and lung, bowel, and bladder problems. Because direct visualization of the individual spinal elements is often required for the above techniques, lengthy incisions and large spinal dissections are required to expose the spinal segments requiring treatment. Even with these major life threatening surgeries, perfect spinal alignment is rarely, if ever, achieved.

What is needed then is a percutaneous apparatus for aligning the spine that possesses few parts and is easy to implant while enabling a gradual restoration of the spinal alignment over a determined period of time so that large and/or sudden forces are not applied to the curved spine. By applying reduced corrective forces over a longer period of time, complications such as bone fracture and nerve damage can be reduced or avoided. Moreover, it would be advantageous in the art of neurosurgery and orthopedic surgery to align a spine with simple percutaneous methods so that endoscopic or minimally invasive techniques can be employed. Additionally, it would be advantageous to access a device for aligning a spine by palpating intact skin to avoid infections.

SUMMARY OF THE INVENTION

The present invention broadly comprises a subcutaneous implantable device for aligning a spine having a plurality of vertebrae including a first brace assembly secured to a first vertebra of the spine, a second brace assembly secured to a second vertebra of the spine, a rod secured by the at least two brace assemblies, the rod arranged for limited sliding movement within the at least two brace assemblies, a gear mechanism attached to the rod, a control means attached to the gear mechanism, and a cable fixedly secured to a third vertebra of the spine by an anchor. The third vertebra is located between the first and second vertebrae, and the cable is arranged for pulling the third vertebra towards the rod.

The present invention also broadly comprises a bone lengthening apparatus including a screw shell secured to a distal portion of said bone, a separation rod including a threaded end arranged to engage the screw shell of the distal portion, the separation rod being arranged to be securable to a proximal portion of the bone and extendable from the proximal portion to the distal portion, and where the proximal portion is separated from the distal portion by a gap, a gear mechanism attached to the separation rod, and a control means attached to the gear mechanism and arranged to rotate the separation rod to widen the gap between the distal and proximal portions of the bone.

A primary object of the invention is to provide a device and method of spinal alignment in which corrective alignment is achieved "gradually" to avoid potential neurological and muscular damage. By "gradually" it is meant over a period of several weeks to several months depending on the severity of the lateral curve.

Another object of the invention is to provide a device for aligning a lateral curve in a spine using simple percutaneous methods and minimally invasive techniques, such as endoscopic techniques.

Yet another object of the invention is to provide a method in which the alignment device may be accessed subcutaneously to reduce the possibility of infection which can occur when a spinal alignment device is connected to a brace outside the body through the skin.

Still another object of the invention is to provide a device for aligning a lateral curve in the spine which can be resorbed into the body where the alignment device, including the balloon and/or anchor and/or a traction cable, is made of bioabsorbable materials.

Another object of the invention is to provide a mechanical device for gradually correcting a spine afflicted with scoliosis subcutaneously.

A further object of the invention is to present a spinal alignment method in which both sides of the spinal column may be subject to an alignment procedure at the same time.

A still further object of the invention is to provide a device for aligning a lateral curve in a spine using a minimum amount of vertebral drilling sites.

Yet another object of the invention is to provide a percutaneous device for aligning a spine including a balloon that can be inflated with bioabsorbable liquids capable of being withdrawn or bioabsorbable material, e.g., bone putty.

Still another object of the invention is to provide a percutaneous device for aligning a spine including a balloon that contains metal vanes which can be deployed against the external cortical surface of a bone to strengthen anchoring capabilities.

An additional object of the invention is to provide a mechanically, hydraulically or electronically operated device including an expandable anchoring mechanism deployable within or around a bone that can be reliably actuated with a pushing or pulling vector force sufficient to controllably alter the temporary or permanent position of a skeletal structure.

An added object of the invention is to supply a bone lengthening assembly for the precise lengthening of a target bone.

These and other objects, features and functions of the present invention will become apparent to those having ordinary skill in the art upon the reading of the following detailed description in view of the drawings and appended claims.

BRIEF DESCRIPTION OF THE SEVERAL VIEWS OF THE DRAWINGS

The nature and mode of the operation of the present invention will now be more fully described in the following detailed description of the invention taken with the accompanying drawing Figures, in which:

FIG. 3 is a cross-sectional view of a hollow bone screw having an outer shell and an inner screw threadably inserted therein;

FIGS. 4 and 4A demonstrate how the inner screw can be separated from the outer shell leaving a lumen as a hollow space along the length of the outer shell;

FIG. 5A is a top view of the stabilizing rod of the assembly of the present invention;

FIG. 5B is a side view of the stabilizing rod showing the receiver formed into the peak that defines a screw hole;

FIG. 5C is a cross-sectional view taken generally along line 5C-5C in FIG. 5B;

DETAILED DESCRIPTION OF EMBODIMENTS OF THE INVENTION

Figure 1:
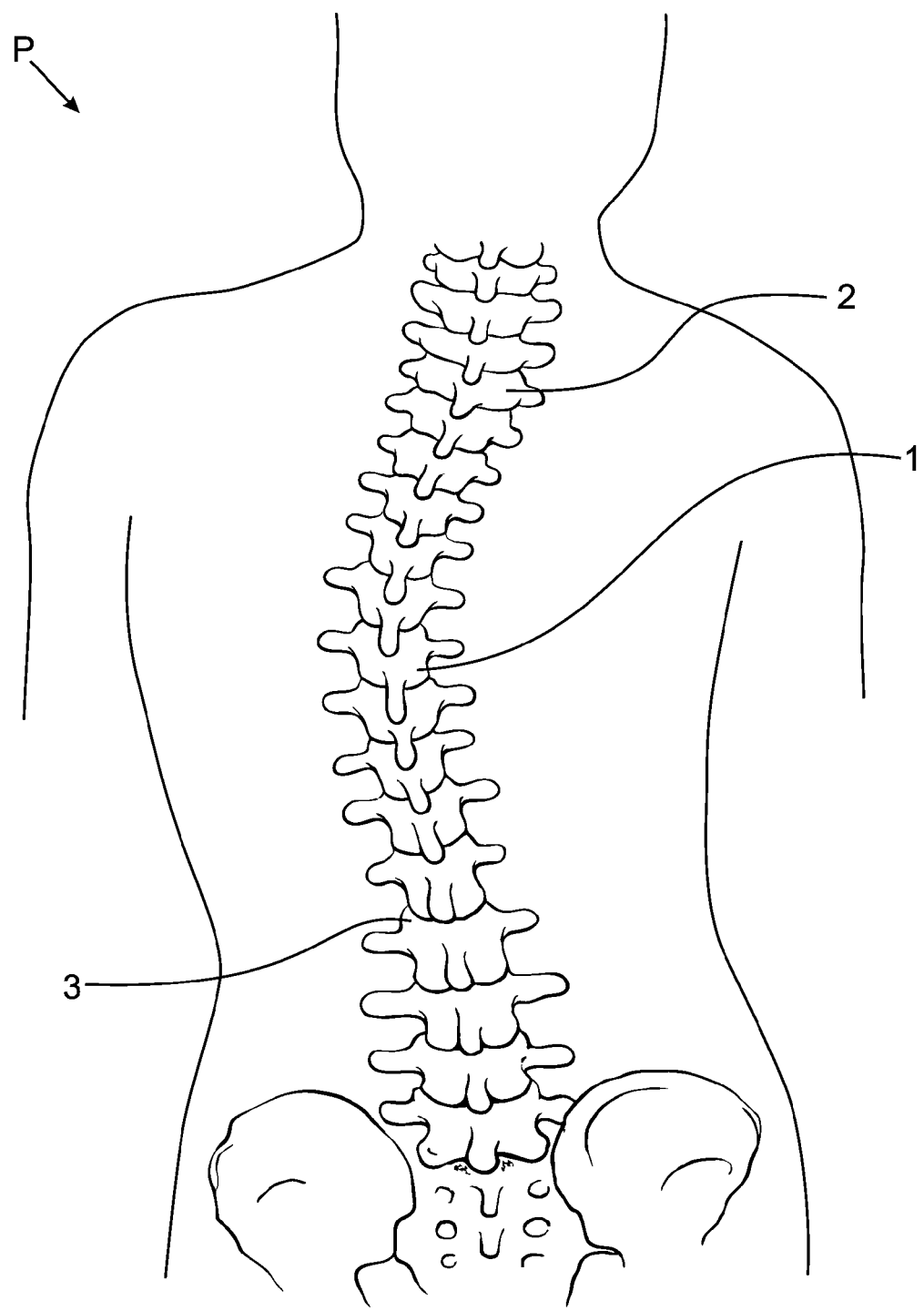
FIG. 1 is a stylized posterior view of a person with a spine afflicted with scoliosis.
Figure 2B:
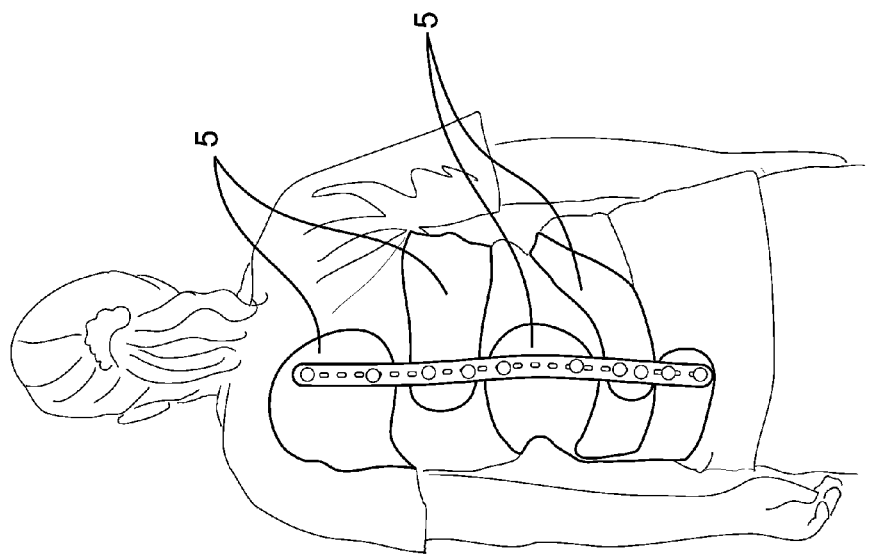
FIG. 2B is a rear view similar to that of FIG. 2A but showing a lighter prior art brace.
Figure 2A:
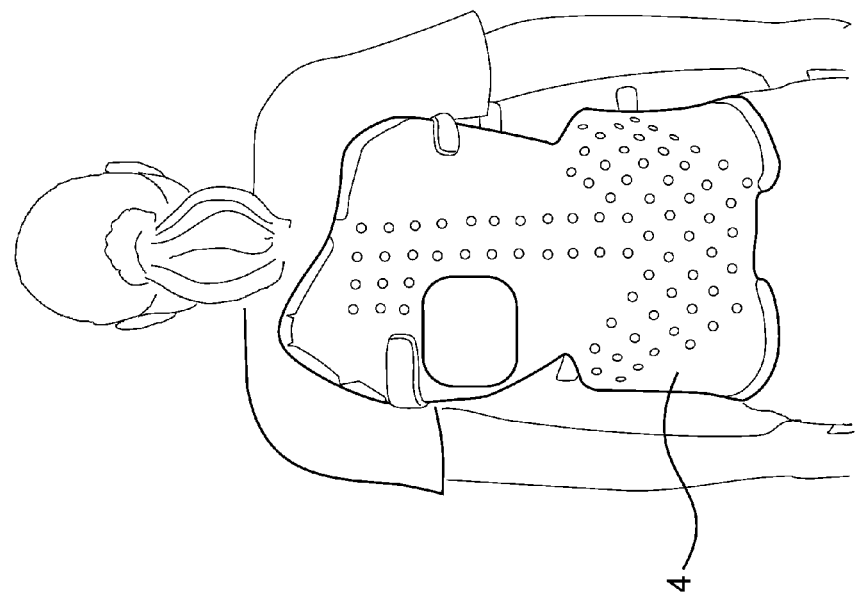
FIG. 2A is a rear view of a person with scoliosis wearing a full body brace as known in the prior art.

At the outset, it should be appreciated that like drawing numbers on different drawing views identify identical structural elements of the invention. It also should be appreciated that figure proportions and angles are not always to scale in order to clearly portray the attributes of the present invention.

While the present invention is described with respect to what is presently considered to be the preferred embodiments, it is understood that the invention is not limited to the disclosed embodiments. The present invention is intended to cover various modifications and equivalent arrangements included within the spirit and scope of the appended claims.

Furthermore, it is understood that this invention is not limited to the particular methodology, materials and modifications described and as such may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. Although any methods, devices or materials similar or equivalent to those described herein can be used in the practice or testing of the invention, the preferred methods, devices, and materials are now described.

FIG. 3 is a cross-sectional view of hollow bone screw 20. The bone screw is used to secure the assembly of the invention to the vertebrae of the patient, as described infra. Outer screw shell 22 is externally threaded with threads 22A to enable it to be screwed into the body of a vertebra as described below. Inner screw 24 is also externally threaded with threads 24A to threadably connect with internal threads 22B of outer screw shell 22. Preferably, cap 24B is attached to the proximal end of inner screw 24. FIGS. 4 and 4A demonstrate how inner screw 24 can be separated from outer shell 22 leaving lumen 26 as a hollow space along the length of outer shell 22. It should be understood that threads 22A and 24A can be omitted.

FIG. 5A is a top view of stabilizing rod 30 ("rod 30"). Preferably, the ends 30A of rod 30 are curved to provide the advantage of being able to move more easily along the spine and longitudinal muscles along the spine. Receiver complex 32 ("receiver 32") extends from the surface of rod 30 to form a peak which defines screw hole 34. FIG. 5B is a side view of rod 30 showing receiver 32 formed into the peak that defines screw hole 34 (not seen in FIG. 5B). Also seen is aperture 36 and set screw 37.

FIG. 5C is a cross-sectional view taken generally along line 5C-5C in FIG. 5B. Set screw 37 is shown set into receiver 32. It can be seen that aperture 36 and set screw 37 have parallel longitudinal axes and both of these axes are substantially perpendicular to the axis 34A of screw hole 34. Annular lip 38 surrounds aperture 36 and set screw 37 and is externally threaded. Set screw 37 engages threaded through-bore 37A (shown in FIG. 6).

Figure 6:
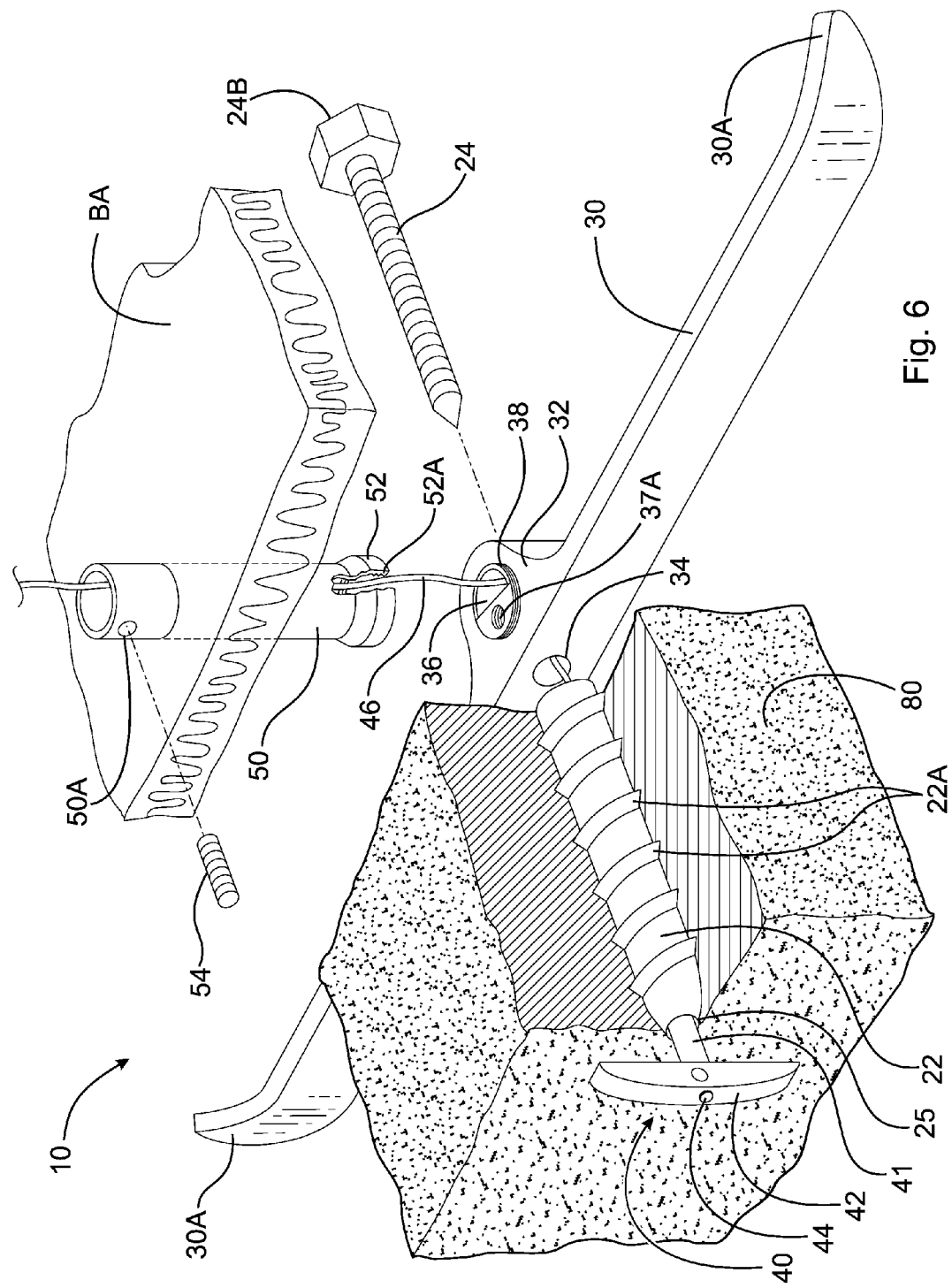
FIG. 6 is side perspective exploded view of the assembly of the present invention attached to a vertebra in the spinal column of the spine to be aligned.

FIG. 6 is a side perspective exploded view of assembly 10 attached to vertebra 80 in the spinal column of the spine to be aligned. Initially, hollow screw 20 is extended into screw hole 34 and is screwed into body 80 of the target vertebra until the distal end point 25 emerges slightly from the distal side, which preferably is at or near the peak of the convex curve of the laterally curved spinal column 1. Inner screw 24 is then removed from outer shell 22 thereby opening lumen 26. Toggle bolt 40 having shaft 41 with a distal end and a proximal end (not seen in FIG. 6) and deployable wings 42 is guided through lumen 26 from the proximal side of vertebra 80 until it extends past distal end point 25 at the distal end hollow screw 20. Preferably, toggle bolt 40 includes pivot attachment 44 to which wings 42 are attached. Wings 42 are deployed (opened out) as shown in FIG. 6 and pulled against the convex side of vertebra 80. Cable 46, attached to the proximal end of shaft 41, extends out the proximal end of lumen 26 and guided into screw hole 34 and up aperture 36. This perpendicular turn is preferably guided by curved wall 36A of aperture 36. Persons having ordinary skill in the art recognize that cable 46 may be threaded from distal end point 25 toward the proximal end of lumen 26 with wings 46 deployed at distal end point 25. In addition, equivalent devices having expanded or expandable components positioned similarly to wings 46 may be used in place of toggle bolt 40 as long as they provide satisfactory support for pulling cable 46 as described below.

Cable 46 is guided through tube 50 which extends posteriorly through back BA. Lip 52 is located at one end of tube 50 and includes internal threads 52A so that tube 50 can be threadably attached to annular lip 38. Set screw 54 is screwed into threaded tube aperture 50A to hold cable 46 in place.

Figure 7:
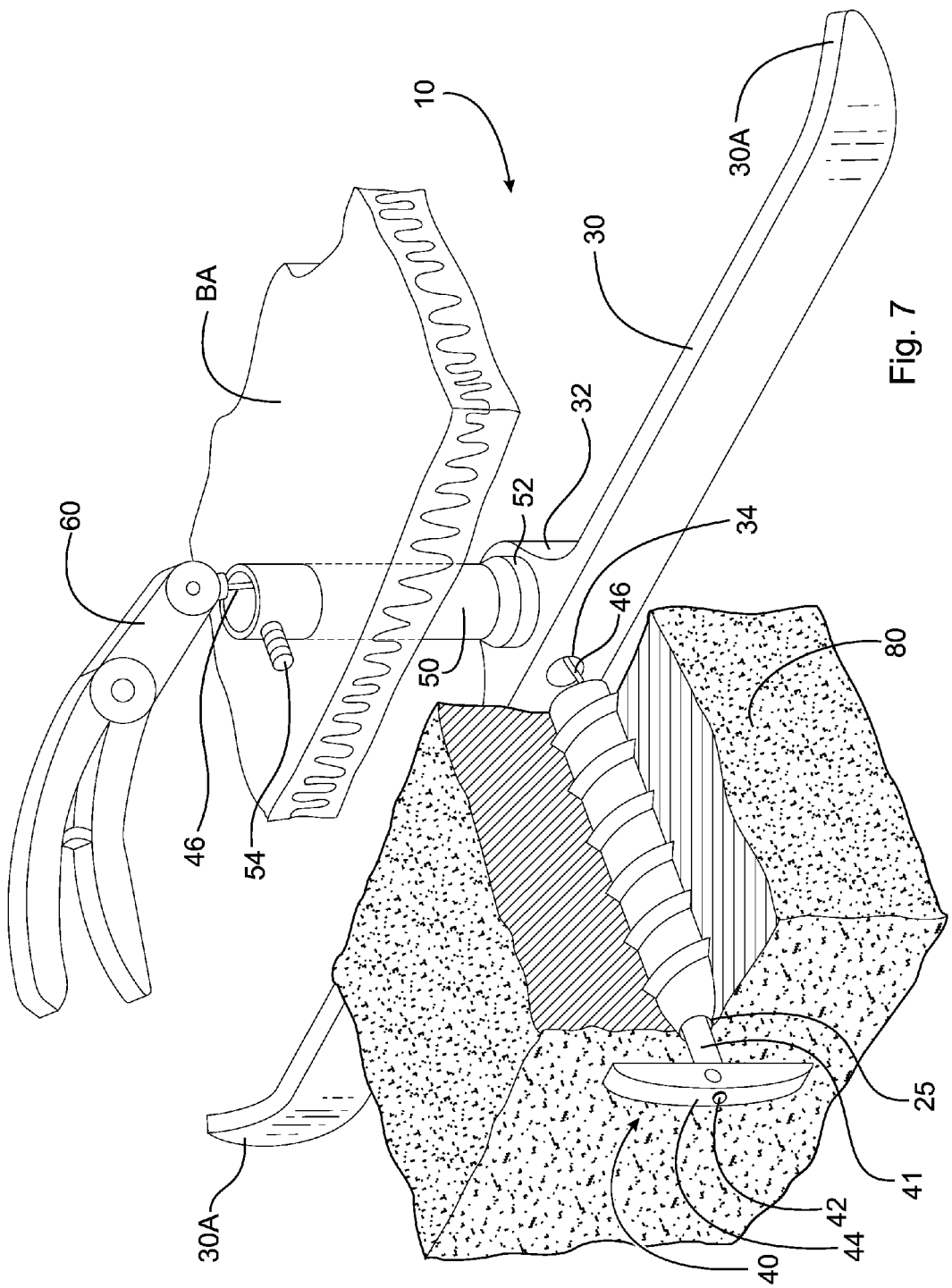
FIG. 7 is a side perspective view of the assembly showing a pulling tool attached to the end of the pulling cable.

FIG. 7 is a side perspective view of assembly 10 showing pulling tool 60 attached to the end of cable 46. Cable 46 has sufficient length to extend from the proximal end of the toggle bolt shaft to outside the back to be attached to pulling tool 60. Examples of pulling tools are winch or reel-type devices, come-along, pliers, screw jacks, or other suitable devices that are able to repeatedly apply a pulling force to cable 46 which pulls the convex apex of laterally curved spinal column 1 at the point where toggle wing 42 contacts vertebral body 80. Tube 50 is threadably attached to annular lip 38. It is understood that other vertebra are positioned above and below target vertebra 80. Because rod 30 is placed along the concave curve of the spine, it is possible that it does not contact vertebra 80 during some or all of the alignment process as is shown in FIG. 7. The perpendicular turn allows the force vectors on cable 46 to be directed out of back BA so that the lungs and surrounding viscera can be avoided.

Figure 8:
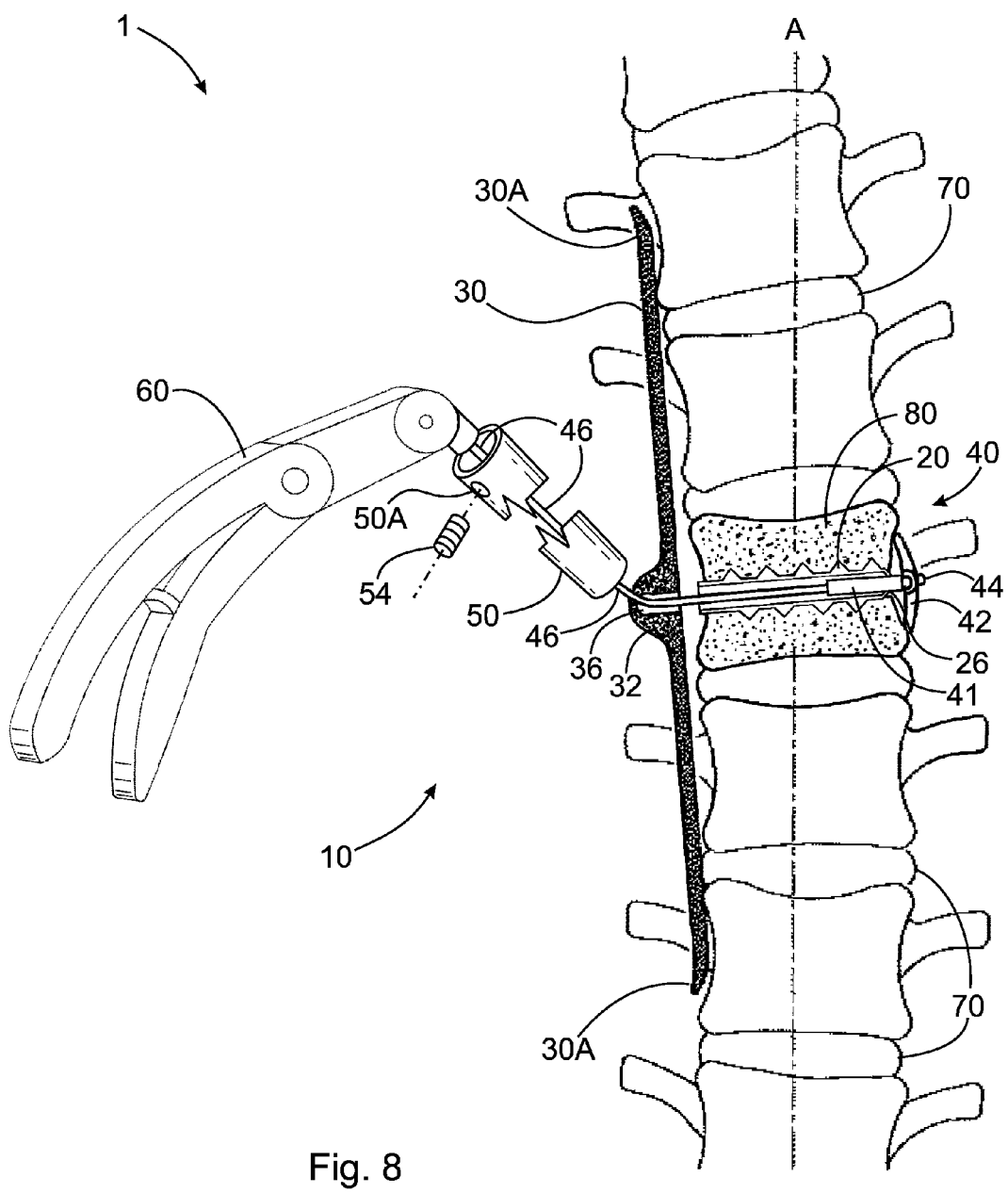
FIG. 8 is an anterior view of a laterally curved spinal column with the alignment assembly in place.

FIG. 8 is an anterior view of laterally curved spinal column 1 with alignment assembly 10 in place as shown in FIG. 7. Axis A represents what the longitudinal axis of spinal column 1 would be when straightened to the ideal anatomical position. Toggle bolt 40 is depicted with deployed wings 42 contacting vertebra 80. Vertebral discs 70 are shown alternately placed within spinal column 1 between each vertebra. The attachment of tube 50 to annular lip 38 is depicted in cut-out form to show cable 46 extending from toggle bolt 40 through lumen 26 and aperture 36 into tube 50. In a preferred practice, tube 50 would be attached to annular lip 38. The further or distal end of cable 46 is attached to pulling tool 60. Rod 30 is placed laterally and longitudinally along spinal column 1. It can be seen that because rod 30 is preferably on the concave side of the lateral spinal curve, it may not contact curved spinal column 1 where cable 46 emerges from spinal column 1 on the concave or proximal side.

Figure 9:
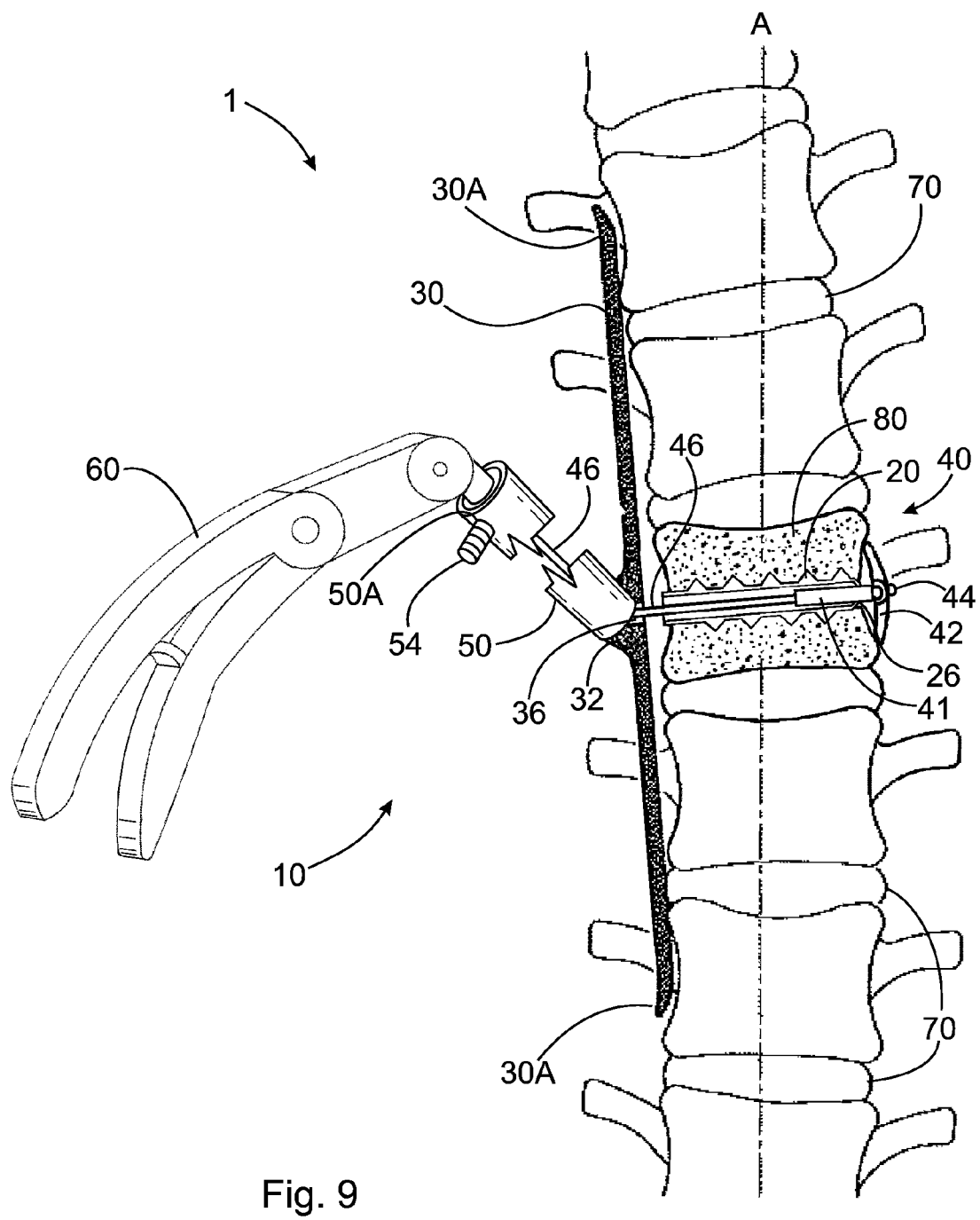
FIG. 9 an anterior view showing the assembly holding the spinal column in place after a pulling procedure.

During the pulling procedure, set screw 54 is loosened or removed from tube aperture 50A. Pulling tool 60 applies pulling force across spinal column 1 onto wings 42. This pulls spinal column 1 against stabilizing rod 30 forcing wings 42 and consequently vertebra 80 toward rod 30 thereby reducing the lateral curve. After sufficient movement, tube set screw 54 is threaded into tube aperture 50A to hold the pulled cable and spinal column in the new straighter position. After a period of time to allow muscles and nerves and spinal column 1 to adjust to the new position, the pulling procedure is repeated with spinal column 1 again being pulled against rod 30 to an even straighter position relative to axis A. FIG. 9 shows assembly 10 after a pulling procedure with tube 50 attached to rod 30 at annular lip 38 (not shown in FIG. 9). By following the sequence of pulling, tightening, and waiting, spinal column 1 is gradually brought closer to proper alignment. By gradual or gradually is meant that alignment may be achieved in a period of as little as one or two days to as long as 6 months, although in mild cases of scoliosis 5-15 minutes to one day may be possible. Normally, an alignment period may range from a week to about three months, but persons having ordinary skill in the art recognize that the length of the alignment period depends on such factors as the severity of the lateral curve, the age of the patient, and the strength of the surrounding neuromuscular structure as well as other factors.

Figure 10:
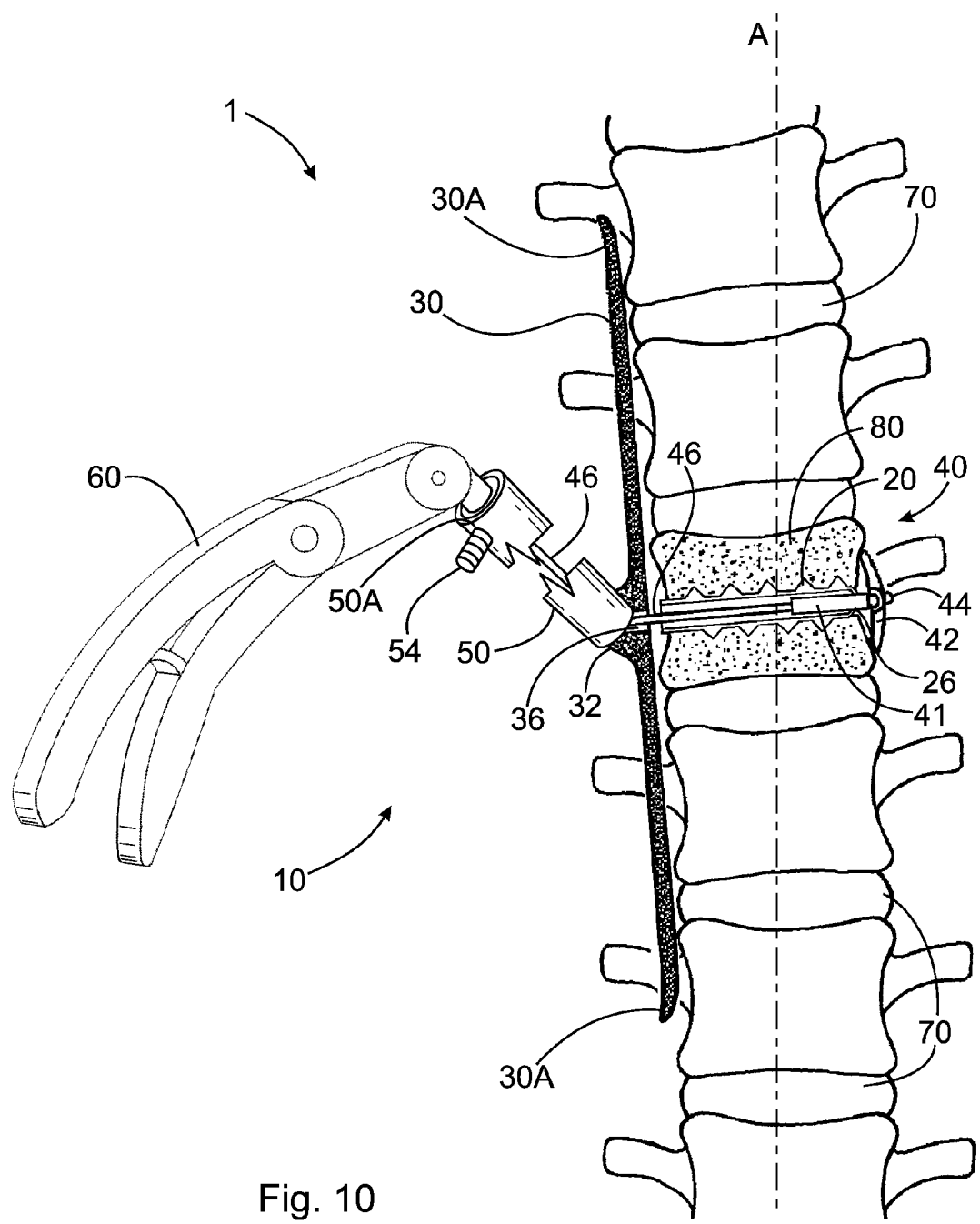
FIG. 10 is an anterior view similar to that of FIG. 9 showing the spinal column moved to a straighter position relative to the axis after a succeeding pulling procedure.
Figure 10A:
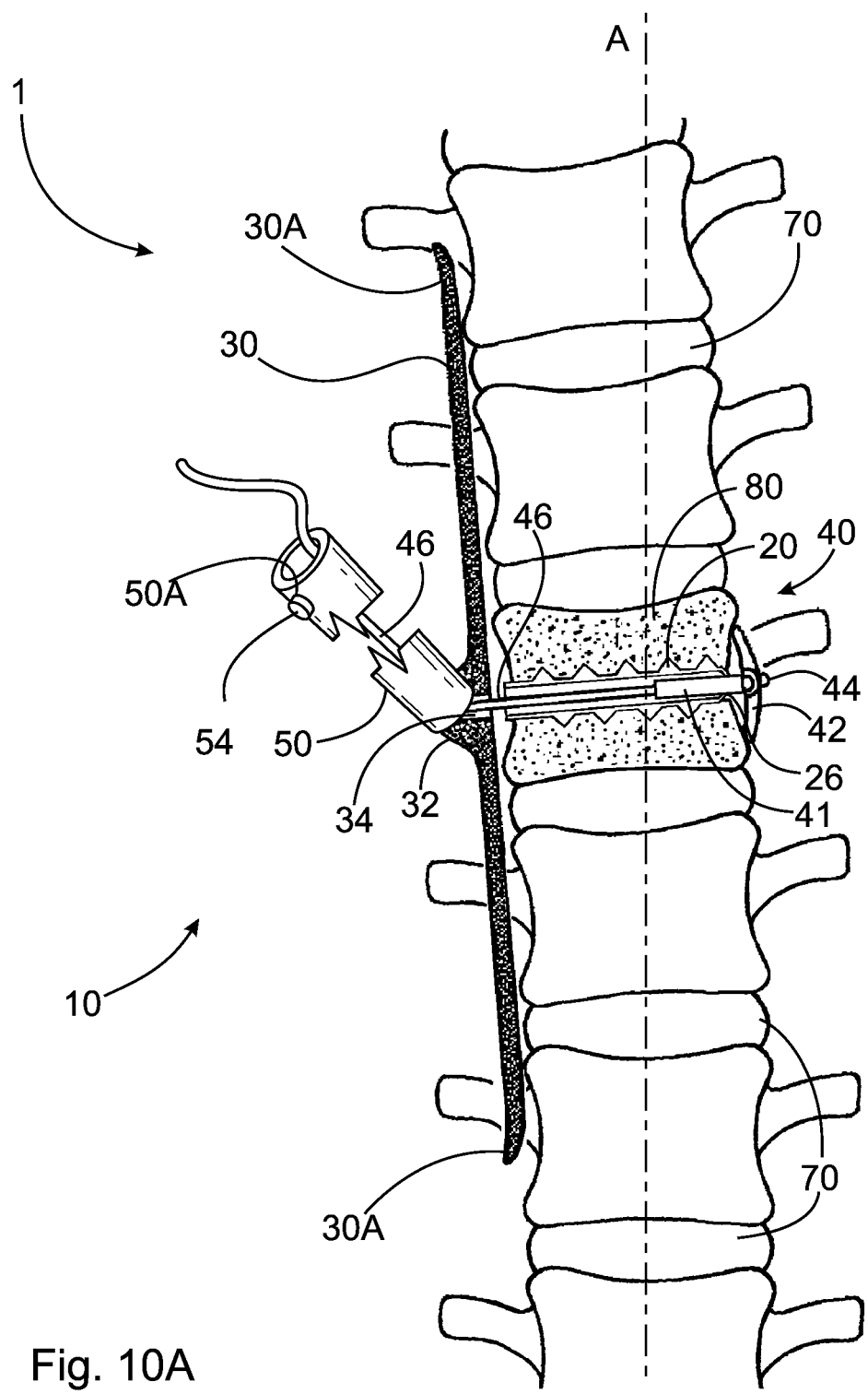
FIG. 10A is an anterior view similar to that of FIG. 10 showing the assembly with the pulling tool removed and the tube set screw screwed into the tube aperture to hold the cable in place between pulling procedures.

FIG. 10 is an anterior view of spinal column 1 moved to a straighter position relative to axis A after a succeeding pulling procedure. Rod 30 is shown closer to spinal column 1 as spinal column 1 is pulled straighter. It can also be seen that curved ends 30A provide an advantage over straight ends in that it allows stabilizing rod 30 to move along spinal column 1 with less if any interference with elements of spinal column 1. FIG. 10A shows assembly 10 with pulling tool removed and tube set screw 54 screwed into tube aperture 50A holding cable 46 in place between pulling procedures.

Figure 11:
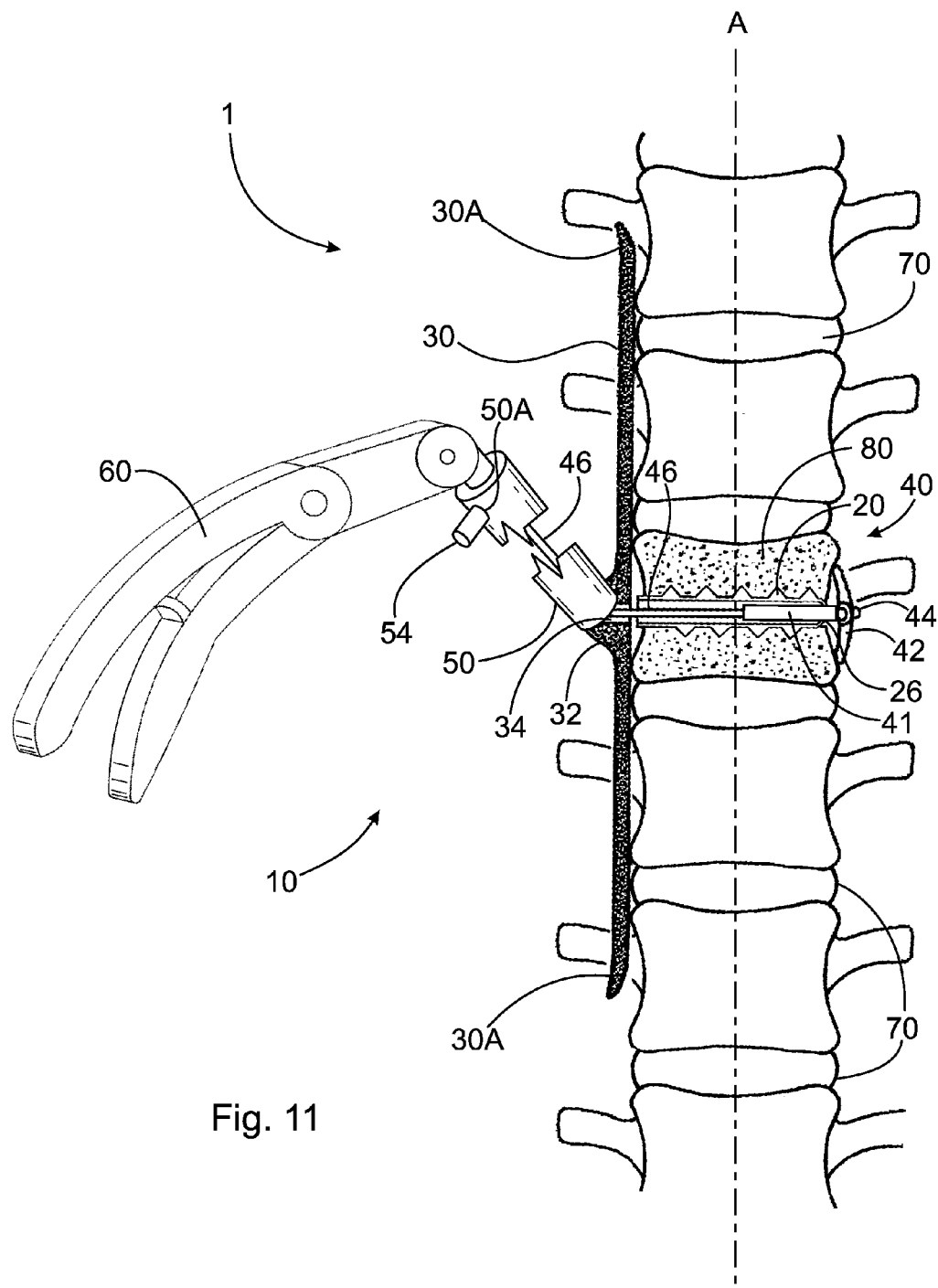
FIG. 11 is an anterior view showing the results of the final pulling procedure in which the lateral curve of the spinal column is significantly reduced if not eliminated.

FIG. 11 is the same anterior view showing the results of the final pulling procedure in which the lateral curve of spinal column 1 is significantly reduced if not eliminated. It can be seen that the middle section of stabilizing rod 30 is pulled close to vertebra 80 at the insertion point of hollow bone screw 20.

Figures 12, 12A:
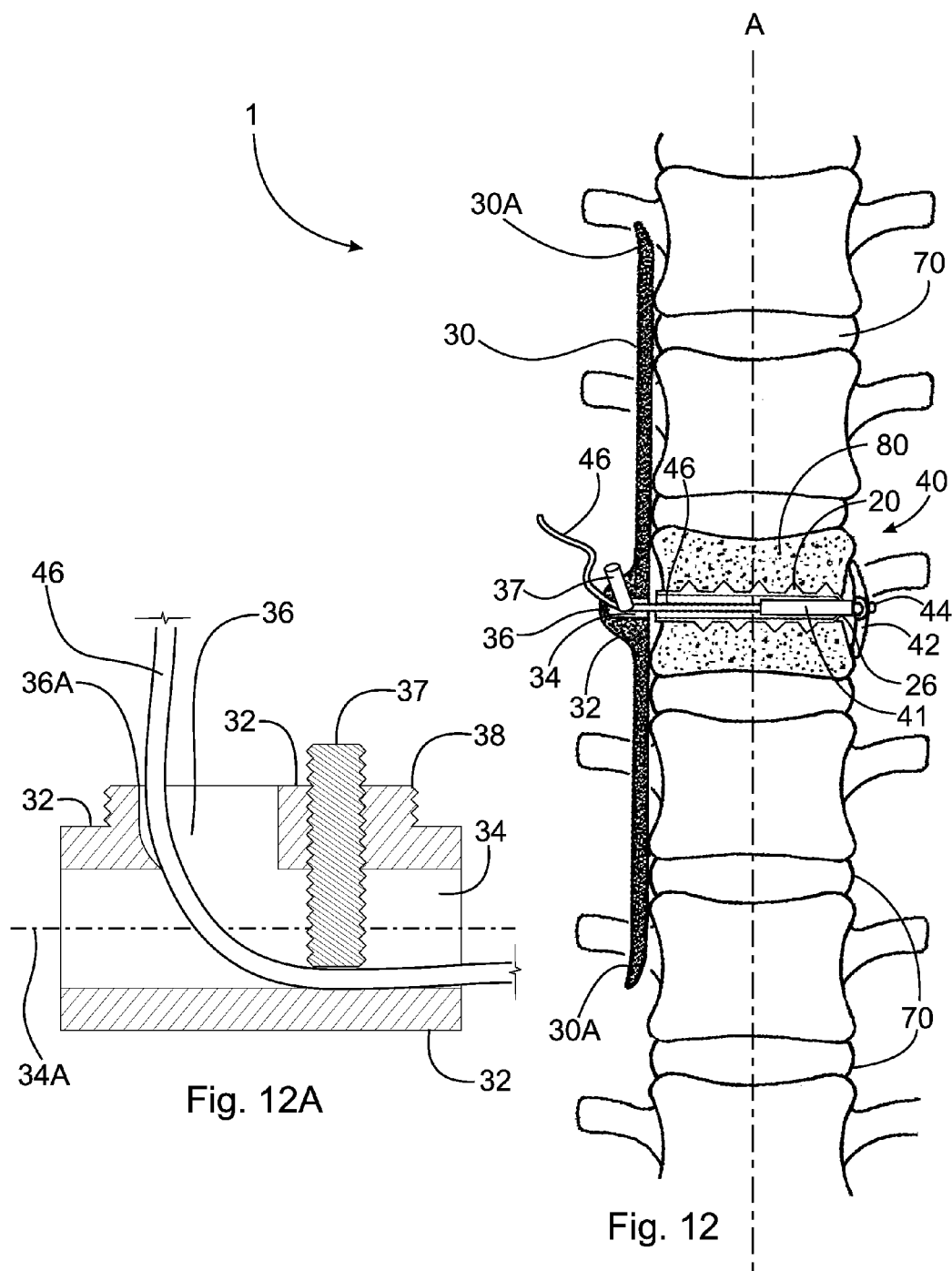
FIG. 12 is an anterior view showing spinal column after the final pulling procedure.
FIG. 12A is a cross-sectional view similar to FIG. 5C showing the set screw holding the cable in place to maintain tension of the assembly after the final pulling procedure.

FIG. 12 is an anterior view showing spinal column 1 after the final pulling procedure. Tube 50 is removed through the back of the patient. Stabilizing rod 30 is left in place holding spinal column 1 in place against toggle bolt wings 42 with the holding force transmitted on cable 46 in lumen 26.

FIG. 12A is a cross-sectional view similar to FIG. 5C in which set screw 37 is shown screwed within screw hole 34 to hold (fix) cable 46 in place under tension after the final pulling procedure. Set screw 37 is screwed in place before set screw 54 is loosened to constantly maintain tension in cable 46 to enable assembly 10 to hold spinal column 1 in the final position. Set screw 37 may be tightened using appropriate conventional or arthroscopic instruments known to those having ordinary skill in the art. Thus, cable 46 is held in place under tension by its attachment to toggle bolt 40 at the distal end and by set screw 37 at the proximal end. After set screw 37 is fixed to cable 46, the remaining "tail" of cable 46 which extends beyond set screw 37 can be cut close to or inside aperture 36. In one embodiment, a cap may be placed over annular lip 38.

In an alternate embodiment, a percutaneous method of spinal alignment requiring no incisions employs puncture wounds to facilitate the placement of deployable bone anchors into or across chosen spinal elements such that tensile forces can be applied to specific areas of the spine thereby facilitating spinal alignment.

To achieve these ends, a standard Jamshidi needle, with removable central stylet, is passed across a chosen spinal element, such as a vertebra, from a direct lateral or a posterolateral approach depending on the desirability of avoiding intervening muscles or other structures.

Figure 13:
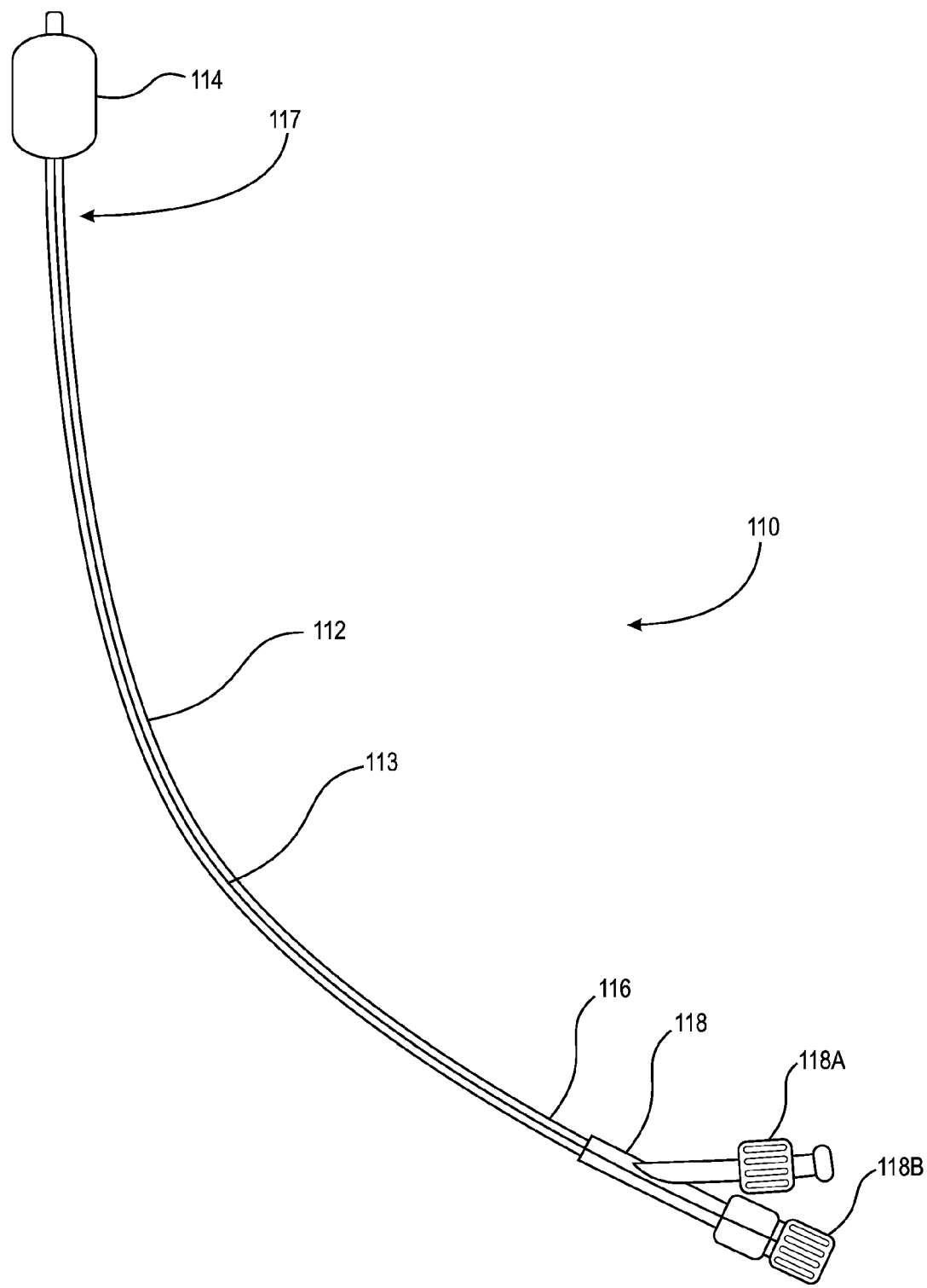
FIG. 13 is a top view of the inflatable balloon bone anchor which is a component of a second assembly utilized in the gradual alignment of a spine with one or more lateral curves.

FIG. 13 is a top view of inflatable balloon bone anchor 110 ("anchor 110") which is a component of assembly 100 (shown in FIG. 16) utilized in the gradual alignment of a spine with one or more lateral curves. Anchor 110 includes hollow tube 112 with inflatable balloon 114 attached at distal end 117 with fluid conduit 118 ("conduit 118") attached to proximal end 116. Optionally, ports 118A and 118B extend from conduit 118 and receive the fluid(s) that may be used to inflate balloon 114 as explained below. Fluids may be introduced into tube 112 and balloon 114 through conduit 118. Preferably, tube 112 and balloon 114 are fabricated from polyglycolic acid or other similar biologically compatible absorbable material which can withstand the tensile or pulling strain created on anchor 110 as described below and resorb into the body well after the alignment procedure is completed. In an example embodiment where balloon 114 is inflatable and deflatable, both ports 118A and 118B can be utilized to allow fluids to pass in and out of balloon 114. In an example embodiment where balloon 114 is dissolvable, only a single port 118A or 118B is needed to allow fluid to pass into balloon 114. In that case, the fluid is introduced and sealed until it dissolves.

Figure 14A:
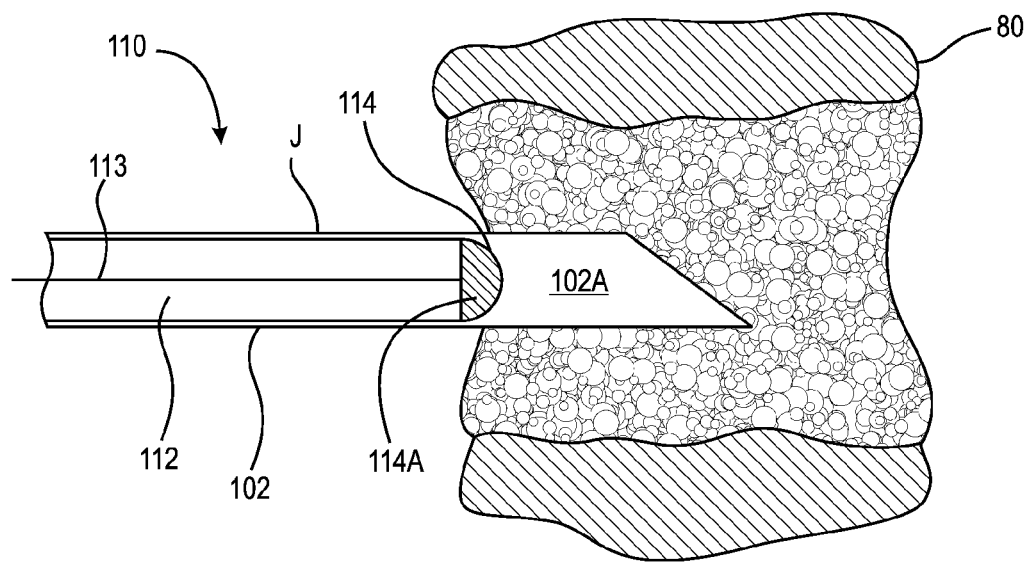
FIG. 14A is a cross-sectional view of a target vertebra in which a Jamshidi needle is used to drill a hole into the target vertebra.
Figure 14B:
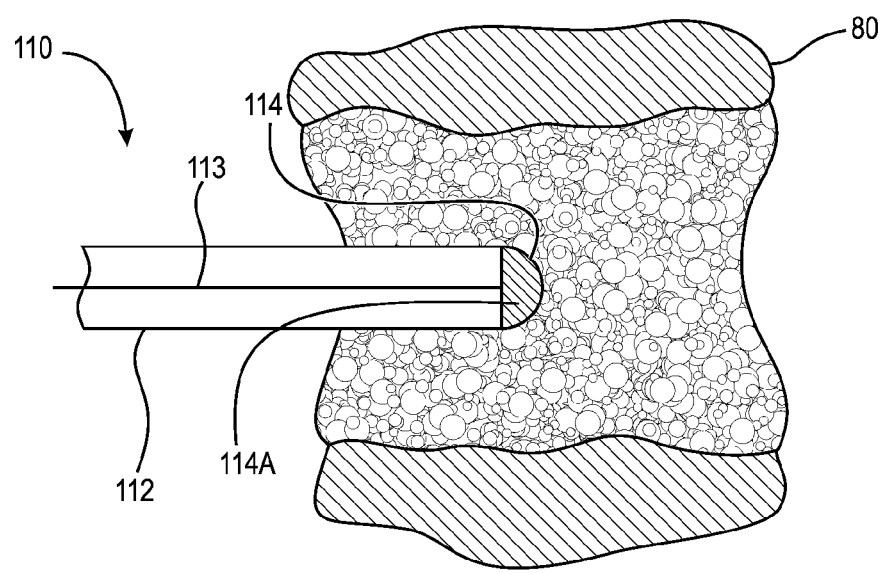
FIG. 14B is the same view as in FIG. 14A depicting the Jamshidi needle withdrawn from around the balloon and tube.
Figure 14C:
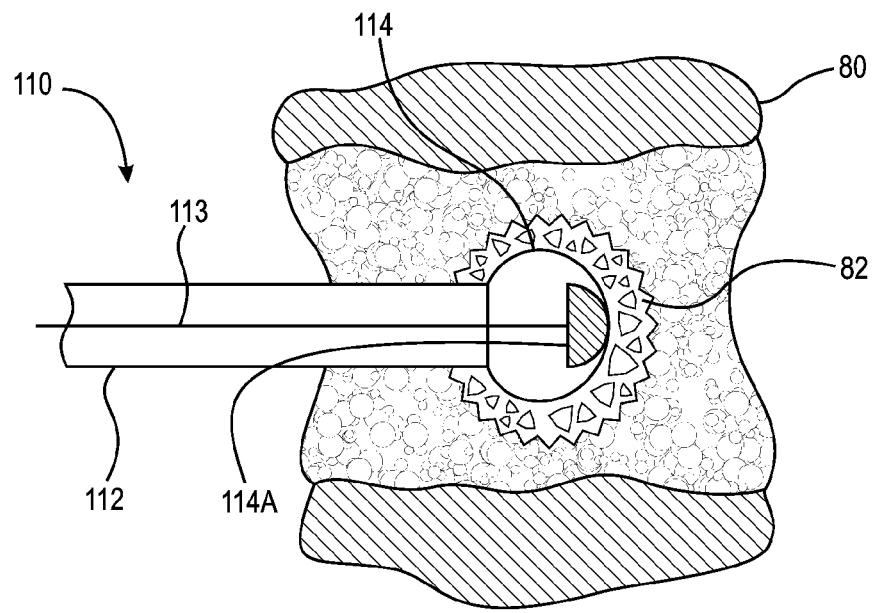
FIG. 14C shows the initiation of the inflation of the inflatable balloon inside the cancellous material at the core of the target vertebra.

FIG. 14A is a cross-sectional view of target vertebra 80 in which a Jamshidi needle 102 ("needle 102") equipped with removable stylet 102A is used to drill a hole into vertebra 80. Inside needle 102 is the distal end 117 of tube 112 with uninflated balloon 114 contacting anchor tip 114A. Cable 113 is seen extending through tube 112 and attached to anchor tip 114A. FIG. 14B is the same view as shown in FIG. 14A with stylet 102A removed from needle 102 and needle 102 withdrawn over tube 112 and from around balloon 114 and tube 112. In one embodiment, needle 102 is withdrawn before conduit 118 is attached to proximal end 116. FIG. 14C shows the initiation of the inflation of balloon 114 inside the cancellous material that forms the core of vertebra 80 while FIG. 14D depicts the withdrawal of anchor tip 114A resulting in the inflated balloon 114 creating and lining a cavity 82 to become embedded within the cancellous bone material.

Figure 14D:
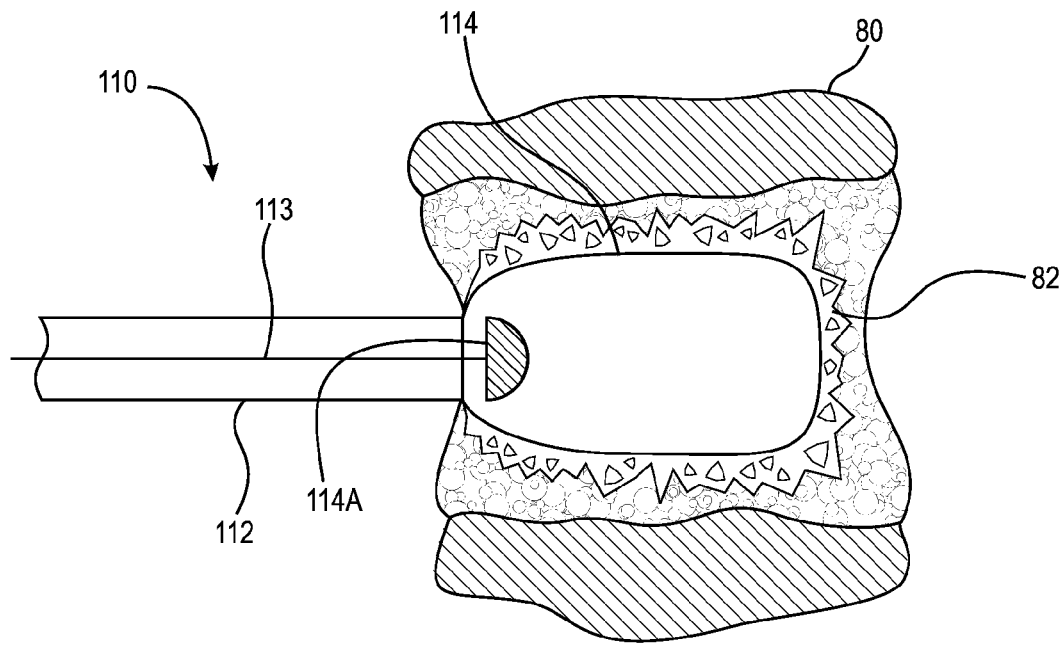
FIG. 14D depicts the withdrawal of the anchor tip resulting in the inflated balloon lining a cavity created within the cancellous bone material.

FIGS. 14C and 14D depict the inflation of balloon 114 through a hydraulic method in which fluid is introduced through ports 118A and/or 118B and passes into balloon 114 through tube 112. As fluid volume increases, balloon 114 increases in size to create cavity 82 in the cancellous material. For temporary anchor fixation, water or saline may be used to inflate balloon 114. Permanent fixation may be achieved with hardenable materials such as bone putty or methyl methylacrylate (MMA) as is known to those having ordinary skill in the art. It should be appreciated that a noncompliant or compliant balloon can be used. If a compliant balloon is used it is made of a hardenable material.

Figure 15A:
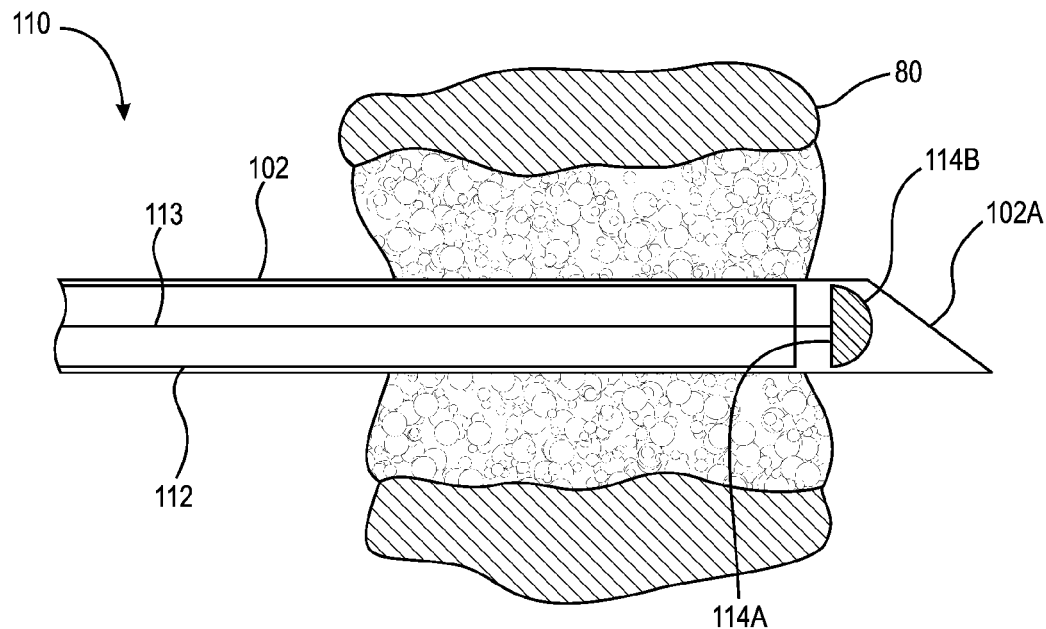
FIG. 15A depicts a second method of attaching the inflatable balloon anchor to a vertebra in which the Jamshidi needle is drilled through the vertebra to create a passage extending through the opposing sides of the vertebra.
Figure 15B:
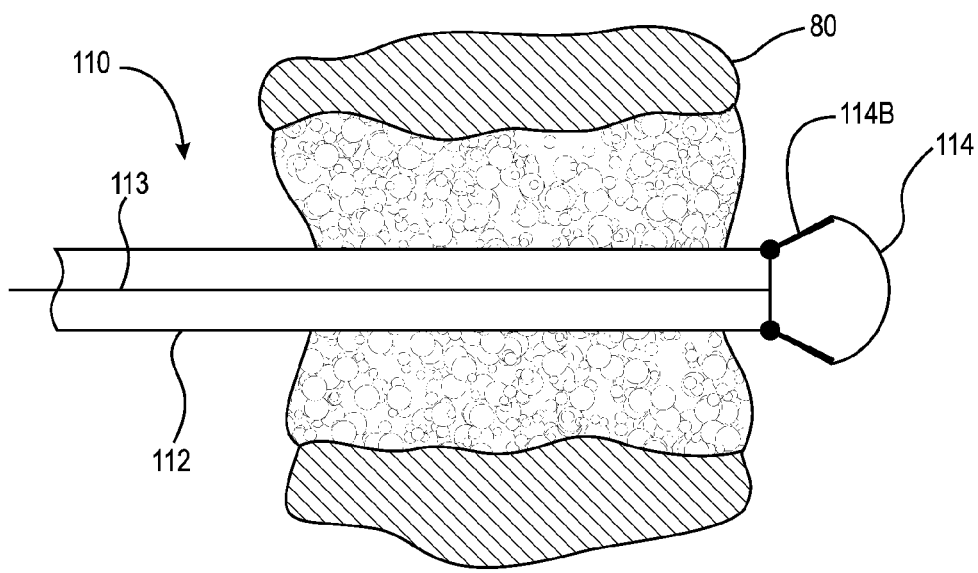
FIG. 15B shows the Jamshidi needle withdrawn from around the inflatable balloon catheter and the balloon starting to inflate.
Figure 15C:
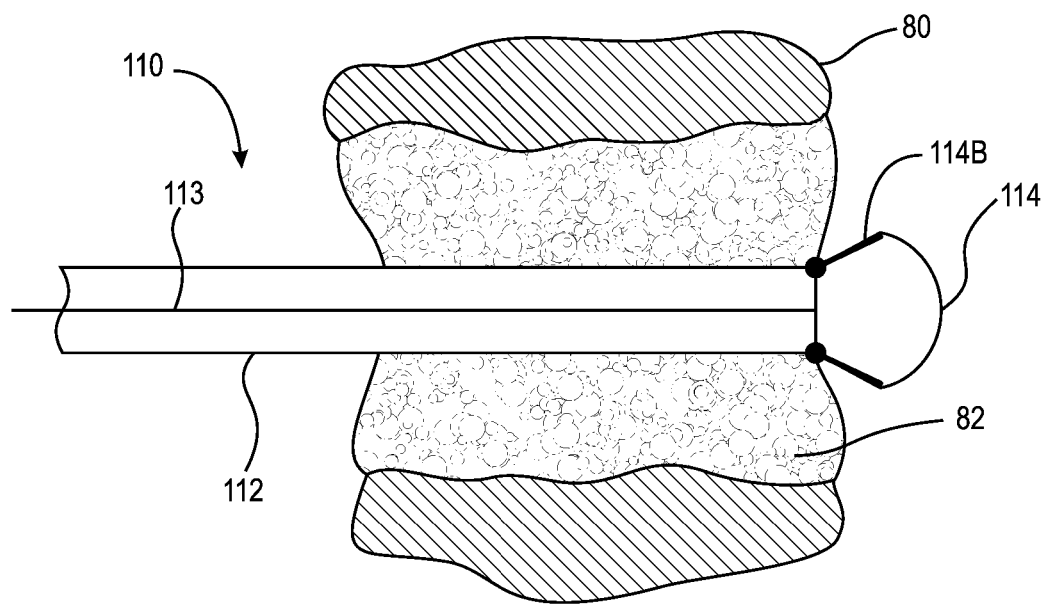
FIG. 15C shows the inflatable balloon drawn against the side of the target vertebra opposing the side where the balloon bone anchor enters the vertebra (proximal side)
Figure 15D:
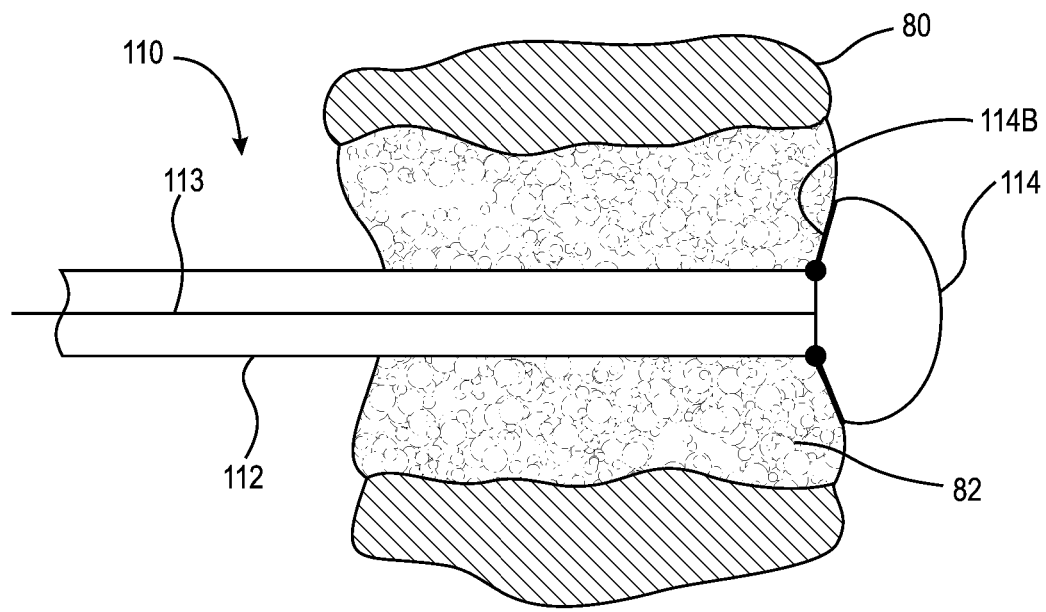
FIG. 15D depicts the fully inflated balloon drawn against the vertebra.

FIG. 15A depicts a second method of attaching anchor 110 to vertebra 80. Needle 102 is drilled or tapped through vertebra 80 to create a passage extending through opposing sides of vertebra 80. Similar to the method described above, it can be seen that anchor 110 is carried inside needle 102 during the drilling process or placed later after stylet is removed. FIG. 15B shows stylet 102A removed and needle 102 withdrawn from around anchor 110 with balloon 114 starting to inflate. FIG. 15C shows balloon 114 drawn against the side of vertebra 80 (distal side) opposing the side where tube 112 enters vertebra 80 (proximal side). FIG. 15D depicts fully inflated balloon 114 drawn against vertebra 80.

FIGS. 15B-15D depict an alternate embodiment of an apparatus for mechanically deploying balloon 114. Array 114B comprises a plurality of arms or vanes operatively attached to the inner surface of balloon 114 and pivotally attached to cable 113. By operatively attached is meant that a component or device is connected either directly or indirectly to a second component and causes that second component to function. For example, each of the plurality of arms in array 114B is operatively attached to the inner surface of balloon 114 and causes balloon 114 to open. When cable 113 is pulled, the arms of array 114B each open causing balloon 114 to inflate. Alternatively, when the balloon is inflated, the arms pivotally deploy. Array 114B may be used to open balloon 114 when greater pulling or traction forces are necessary during the aligning process as explained below. It is recognized that the mechanical inflation method may be used to form cavity 82 and embed balloon 114 as seen in FIGS. 14C and 14D. Conversely, the hydraulic method described above may be used to inflate balloon 114 and draw it toward vertebra 80 as seen in FIGS. 15C and 15D.

Figure 16:
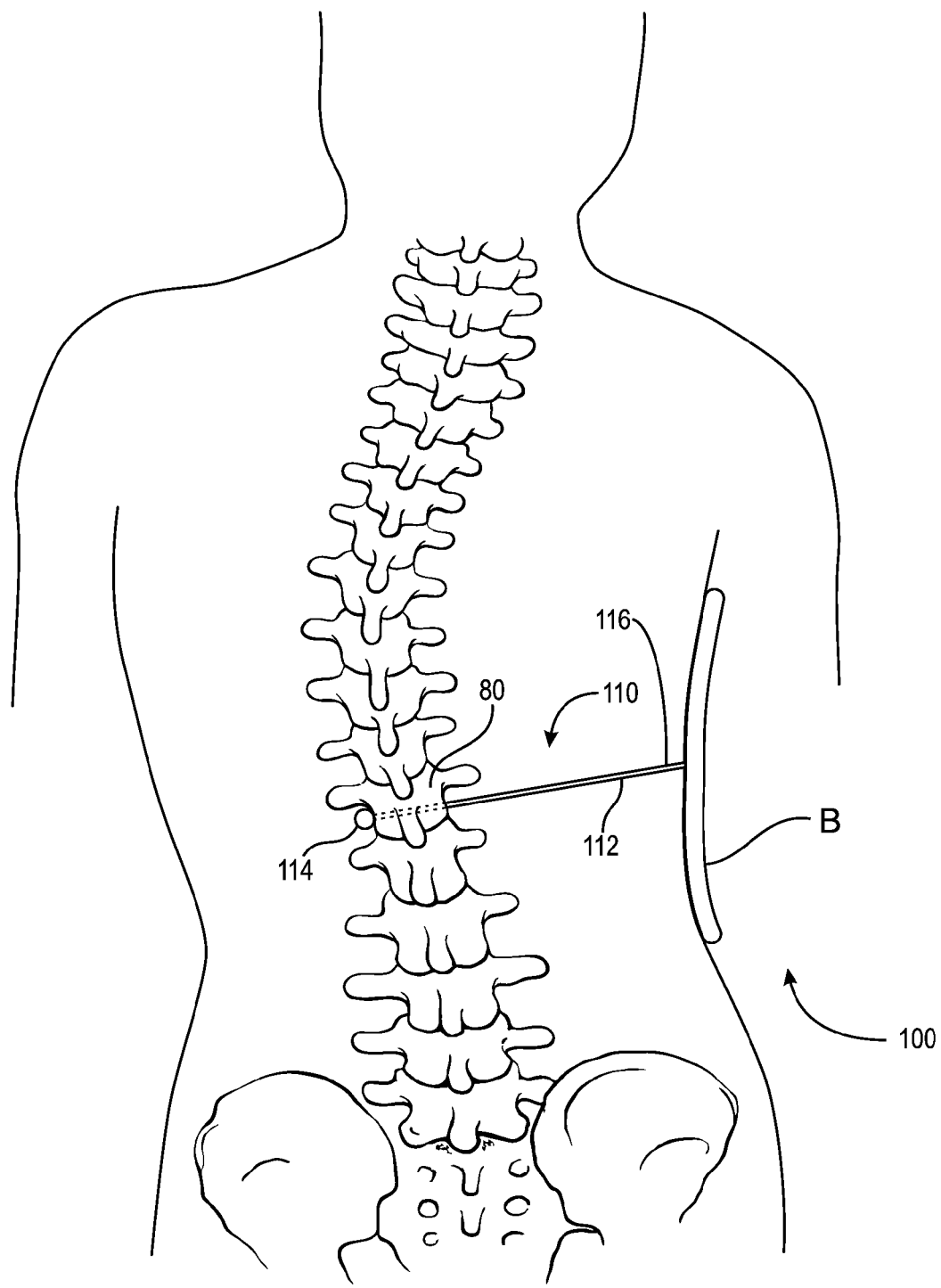
FIG. 16 is a schematic posterior view of the inflatable balloon catheter attached to an external leverage support to form the second embodiment of the present invention.

FIG. 16 is a schematic posterior view of anchor 110 attached to external leverage support B to form assembly 100. In the posterior view shown, tube 112 extends through vertebra 80 with inflatable balloon 114 drawn against a side of vertebra 80 on the convex side of the lateral curve of the spinal column. After balloon 114 is inflated, tube 112 is releasably attached to external leverage support B, in this case external body brace ("brace B") similar to that seen in FIG. 1 and otherwise described above. Proximal end 116 is attached to brace B. To effect the attachment outside the body, a small incision may be made to pass tube 112 through the skin and releasably attach it to brace B. Attachment may be made similar to that seen above with assembly 10 in which cable 46 is pulled and tied against stabilizing rod 30. Pulling tools such as come-alongs, winches, pliers, etc., attached to proximal end 116 may be used.

Because the attachment to vertebra 80 is percutaneous and reversible, multiple points of attachment can be selected to resolve multiple curve issues as well as to spread corrective force over more than target vertebra 80 so that excessive force on a single cable is not required. Partial external braces B may be used opposite each series of assemblies 100 to direct the required pulling force more precisely. This provides the advantage of obviating the need for the large external braces presently in use. In a preferred embodiment, the braces may have movable pads or points of contact to prevent applying the pulling force at the same site on the skin.

Figure 17:
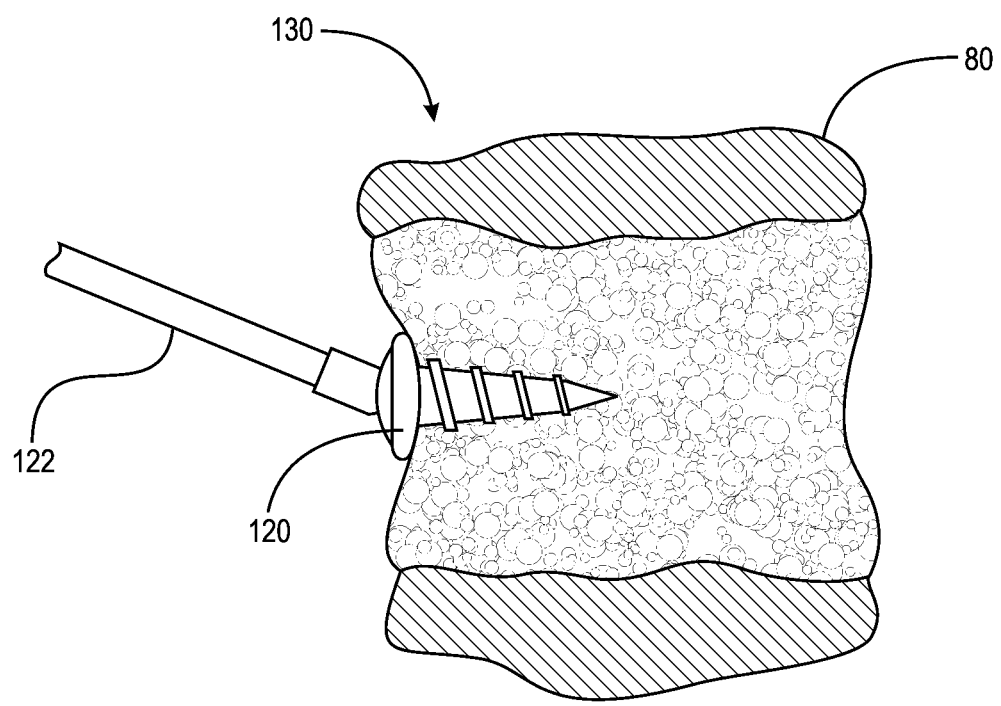
FIG. 17 is a partial cross-sectional view of a bone screw embedded into a vertebra and attached to a strut.

FIG. 17 is a cross-sectional view of bone screw 120 embedded into vertebra 80 and attached to strut 122. Bone screw 120 and strut 122 are components of bone screw-strut construction 130 shown in FIG. 18B. This bone screw-strut construction 130 ("construction 130") can be used to apply a pushing force on the lateral curve by turning strut 122, which is attached to brace B', toward embedded bone screw 120, thereby pushing the lateral curve into alignment. Preferably, bone screw 120 is attached to strut 122 by a hinge or some other polyaxial connection to allow different vector angles of force to be applied to bone screw 120 as it pushes on the lateral curve.

Figure 18A:
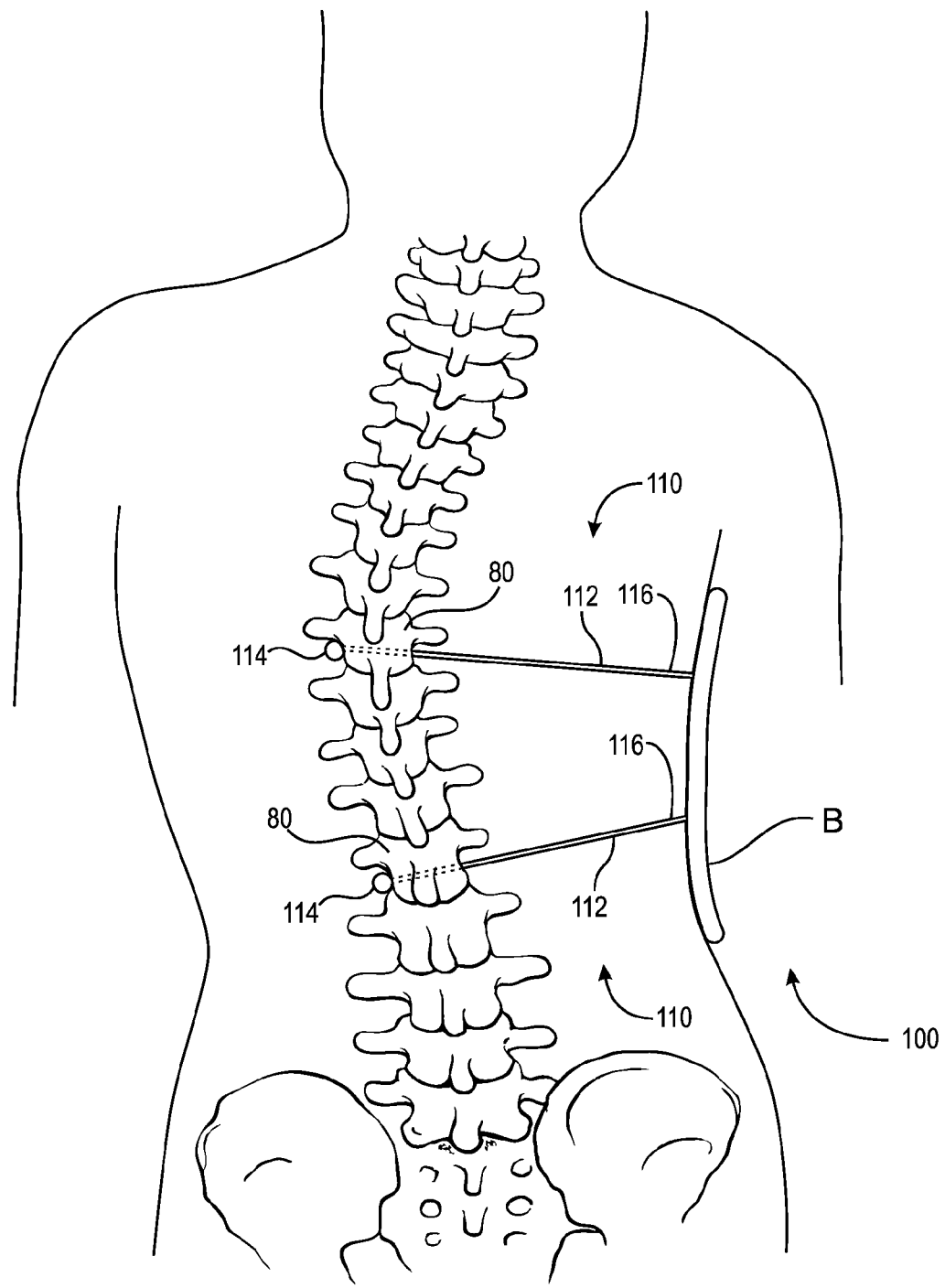
FIG. 18A is a schematic view of the use of two balloon anchor assemblies to pull the spinal column into alignment.

FIG. 18A is a schematic view of the use of two assemblies 100 to pull the spinal column into alignment. It can be seen that anchors 110 are attached to vertebrae 80 with balloons 114 contacting vertebrae 80 on the convex side of the lateral curve. This arrangement provides the advantage of reducing the forces applied to the components of bone anchor 110 as well as to the spinal column itself.

Figure 18B:
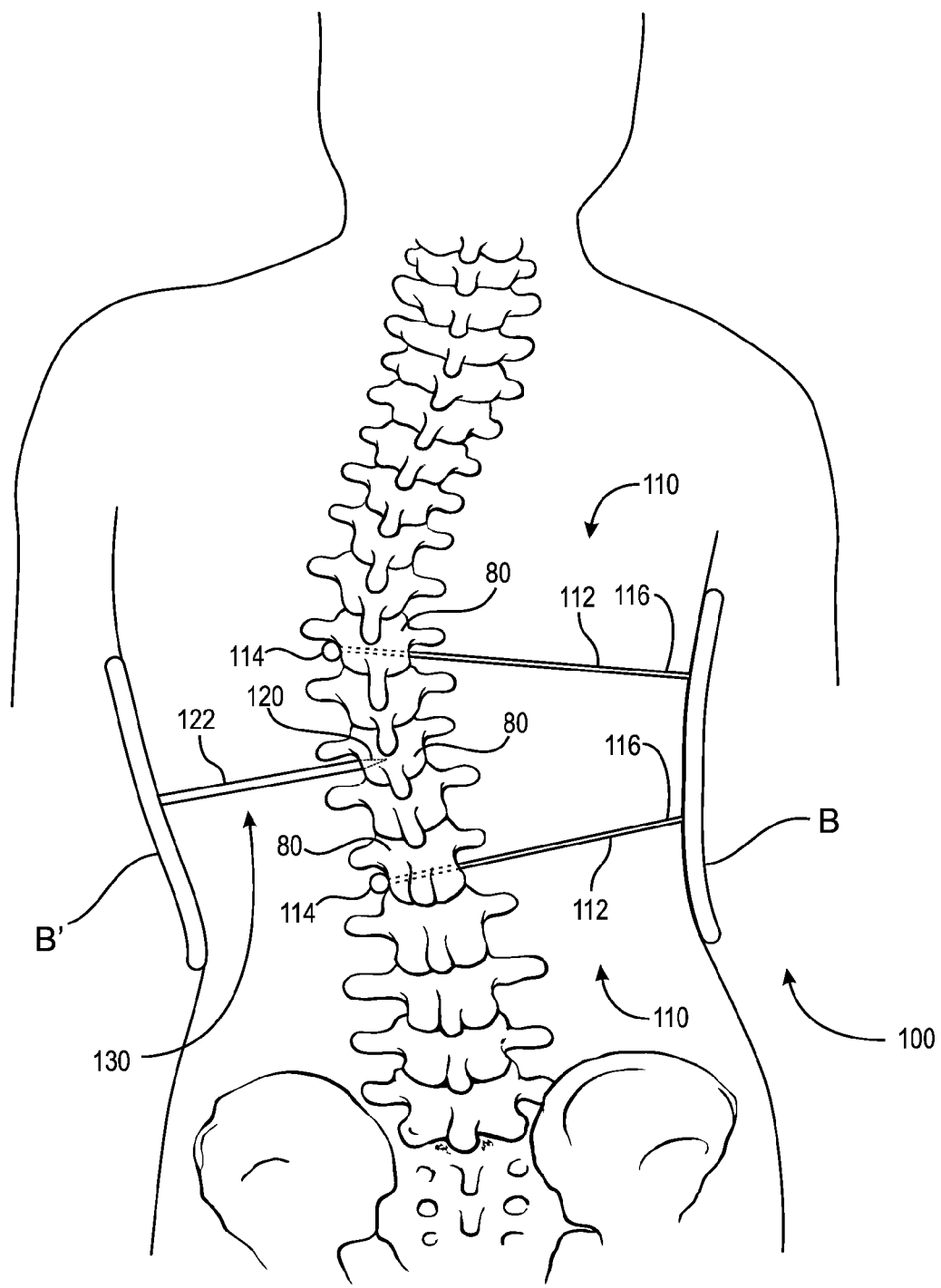
FIG. 18B depicts schematically the use of the bone screw construction with one or more balloon anchor assemblies to combine both pulling and pushing forces to simultaneously apply corrective pressure on both sides of the lateral curve.

FIG. 18B schematically depicts the use of bone screw construction 130 with one or more assemblies 100 to combine both pulling and pushing forces to apply corrective forces on both sides of the lateral curve. Construction 130 is attached to brace B' on the opposite side of the spine from assemblies 100. It is recognized that brace B' may be the same or a different external support than support B attached to assemblies 100. Bone screw 120 may be used to push the lateral curve into alignment by screwing strut 122, threadably attached to brace B', toward the convex side of the lateral curve and thereby pushing it into alignment. FIG. 18B also shows two assemblies 100 pulling two portions of the same lateral curve into alignment demonstrating the attachment of assemblies 100 to multiple points on the spine.

Assemblies 100 are used in a manner similar to that used for assembly 10 described above. With anchors 110 attached to target vertebra 80, and proximal ends 116 attached to brace B, tubes 112 are pulled toward brace B to pull the lateral curve closer to alignment. After the pulling process, tubes 112 are attached to brace B in such a way so as to hold anchors 110 in the pulled position, thereby holding the lateral curve in its new position closer to the desired alignment. The pulling process and the results of the pulling process can be observed with MRI, x-rays, etc. to determine how much to pull anchors 110 each time. By repeating the "pull-tie off" process, the lateral curve can gradually be brought into or closer to alignment without disrupting surrounding tissue and nerves. Similarly, bone construction 130 may supplement assemblies 100 to gradually push the spine into the desired alignment Once the desired spinal alignment is achieved over a period of time, much like braces are used to align teeth, the spine can be fused using endoscopic techniques and the deployed anchors can be contracted and removed or dissolved into the body. Alternatively, percutaneous alignment could be maintained until skeletal maturity is reached, potentially obviating the need for surgery entirely.

Figure 19:
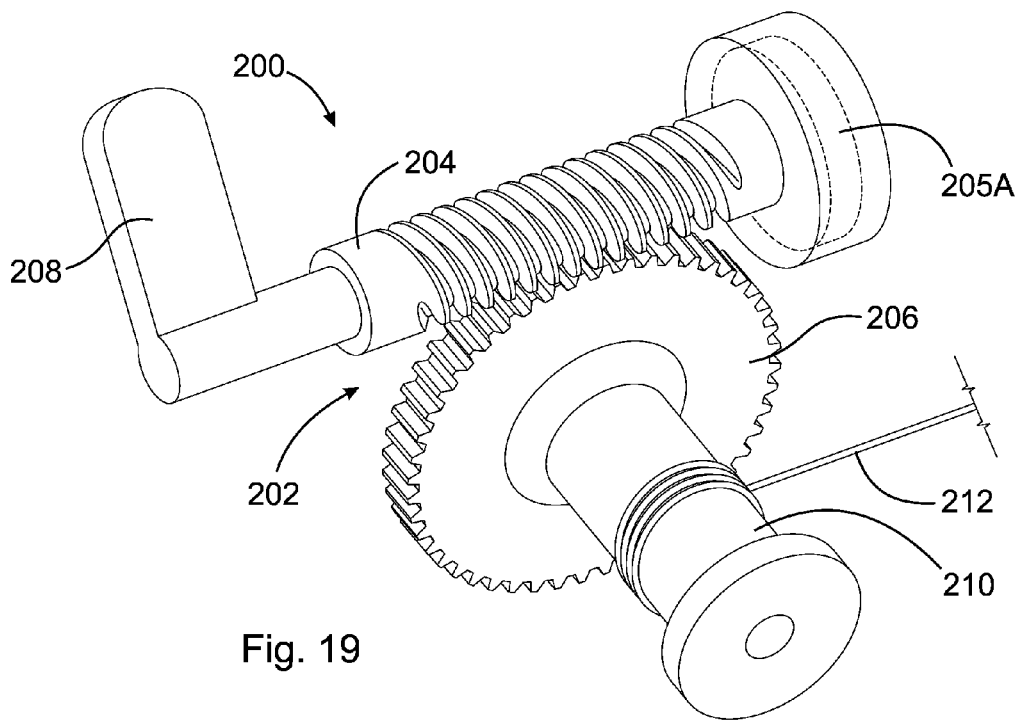
FIG. 19 is a top perspective view of a winding means component of a second alternate embodiment of an assembly for performing a gradual lateral spinal alignment of a spine.

FIG. 19 is a top perspective view of a winding means component of a second alternate embodiment of assembly 200 for performing a gradual lateral spinal alignment of a spine. In the configuration shown, the winding means is in the form of ratcheting mechanism 202, for example, a worm gear, which includes screw 204 that interacts with wheel 206. It should be appreciated that screw 204 could be a worm screw and that wheel 206 could be a worm wheel. Wheel 206 includes stem 210 which holds or retains cable 212. Control lever 208 acts as a control means and is operatively attached to screw 204 to turn screw 204 a predetermined amount when pressed. By "operatively attached" it is meant that a component or device is connected either directly or indirectly to a second component and causes that second component to function, e.g., turn a predetermined amount. As can be seen in FIG. 19, when screw 204 turns, wheel 206 also rotates which in turn rotates stem 210 to wind cable 212. It should be appreciated that due to the frictional relationship between screw 204 and wheel 206, wheel 206 cannot rotate worm screw 204. Spring means 205A is provided to enable lever 208 to rebound to its starting position so that lever 208 can only be moved a predetermined amount when pressed. Spring means 205A is in the form of a torsion spring, for example.

Figure 20:
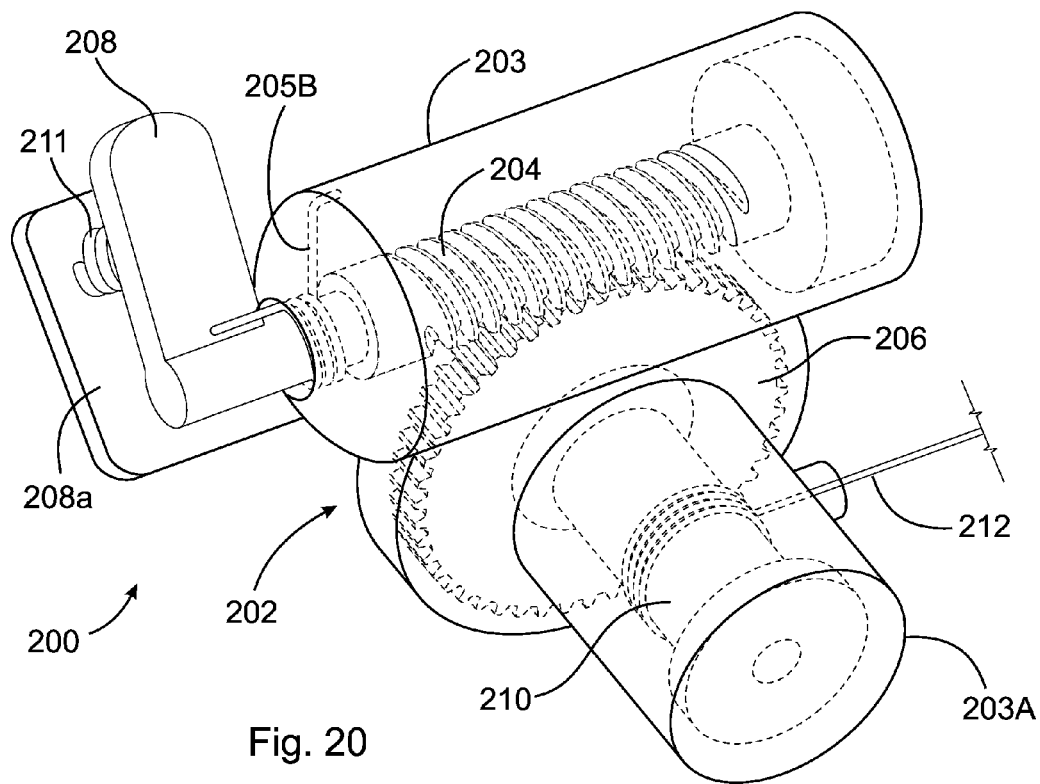
FIG. 20 is a top perspective view of the worm gear enclosed in a housing.

FIG. 20 is a top perspective view of ratcheting mechanism 202 enclosed in housing 203. It is apparent to those having skill in the art that housing 203 may be a single unit enclosing ratcheting mechanism 202 or may include separately elements that enclose the individual components of ratcheting mechanism 202, such as housing 203A enclosing stem 210 as seen in FIG. 20. It should be appreciated that housing 203 can be made of any suitable casing for example, a silicone elastomer. Preferably, spring means 205B is included to enable lever 208 to rebound to its starting position creating a ratchet effect so that lever 208 can only be moved a predetermined amount when pressed. Spring means 205B can be in the form of a coil spring attached to housing 203 in which lever 208 is caused to return to a starting position. Lever 208 may rebound to a starting position off coil spring 211 attached to rebound board 208A. Persons having ordinary skill in the art recognize that although FIGS. 19-20 depict different spring means that act to return lever 208 to a starting position, preferably, only one spring means is utilized in any one particular ratcheting mechanism 202.

Figure 21A:
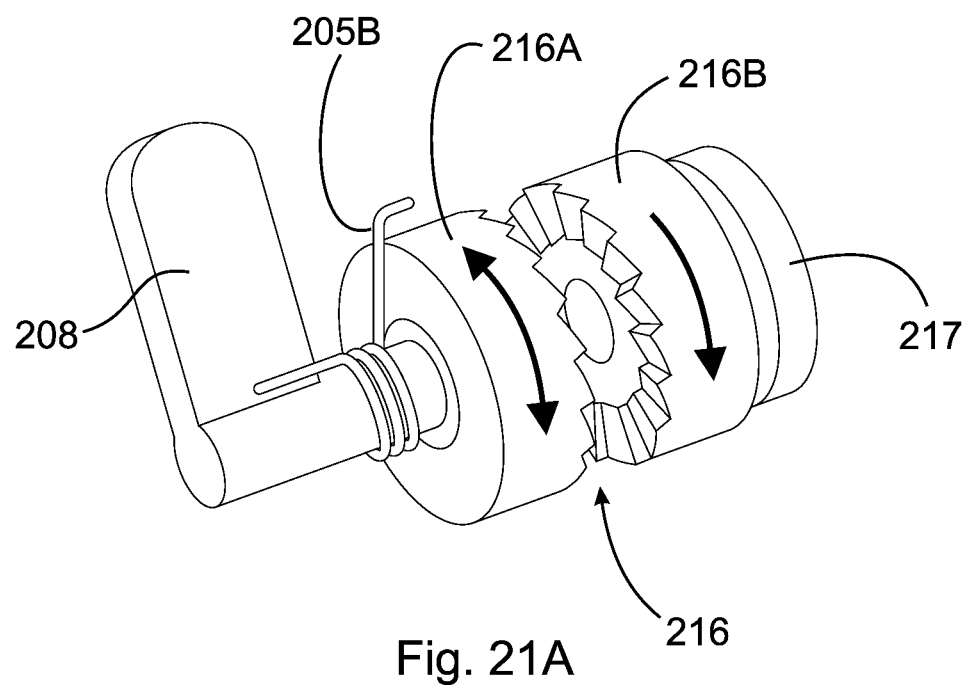
FIG. 21A is a top perspective view of a ratchet assembly used as an alternate form of a winding means in the second alternate assembly for performing gradual spinal alignments.
Figure 21B:
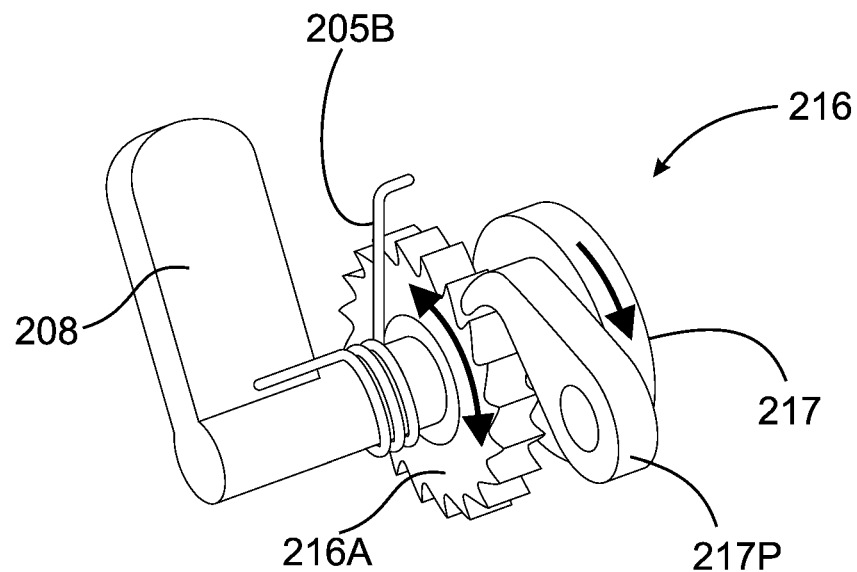
FIG. 21B is a top perspective view of a ratchet assembly used as an alternate form of a winding means in the second alternate assembly for performing gradual spinal alignments.

The winding means may be a ratchet mechanism used to control the rotation of stem 210 through ratcheting mechanism 202 or directly through control of ratchet assembly 216 as shown in FIGS. 21A and 21B. In FIG. 21A, control lever 208 is operatively attached to ratchet gear 216A which engages ratchet gear 216B to rotate ratchet gear 216B in a single direction. In FIG. 21B, control lever 208 is operatively attached to a single ratchet gear 216A and control lever 208 can rotate ratchet gear 216A in a single direction via pawl 217P. Pawl 217P is connected to housing 203 surrounding assembly 216 (shown in FIG. 20). Spring 217 acts to maintain rotational tension in ratchet assembly 216 to return lever 208 to its starting position. Persons having ordinary skill in the art recognize that a worm screw, such as screw 204, may be attached to ratchet assembly 216 to enable ratcheting mechanism 202 to be rotated a predetermined amount and thus pull cable 212 a predetermined amount with each press of control lever 208.

Figure 22:
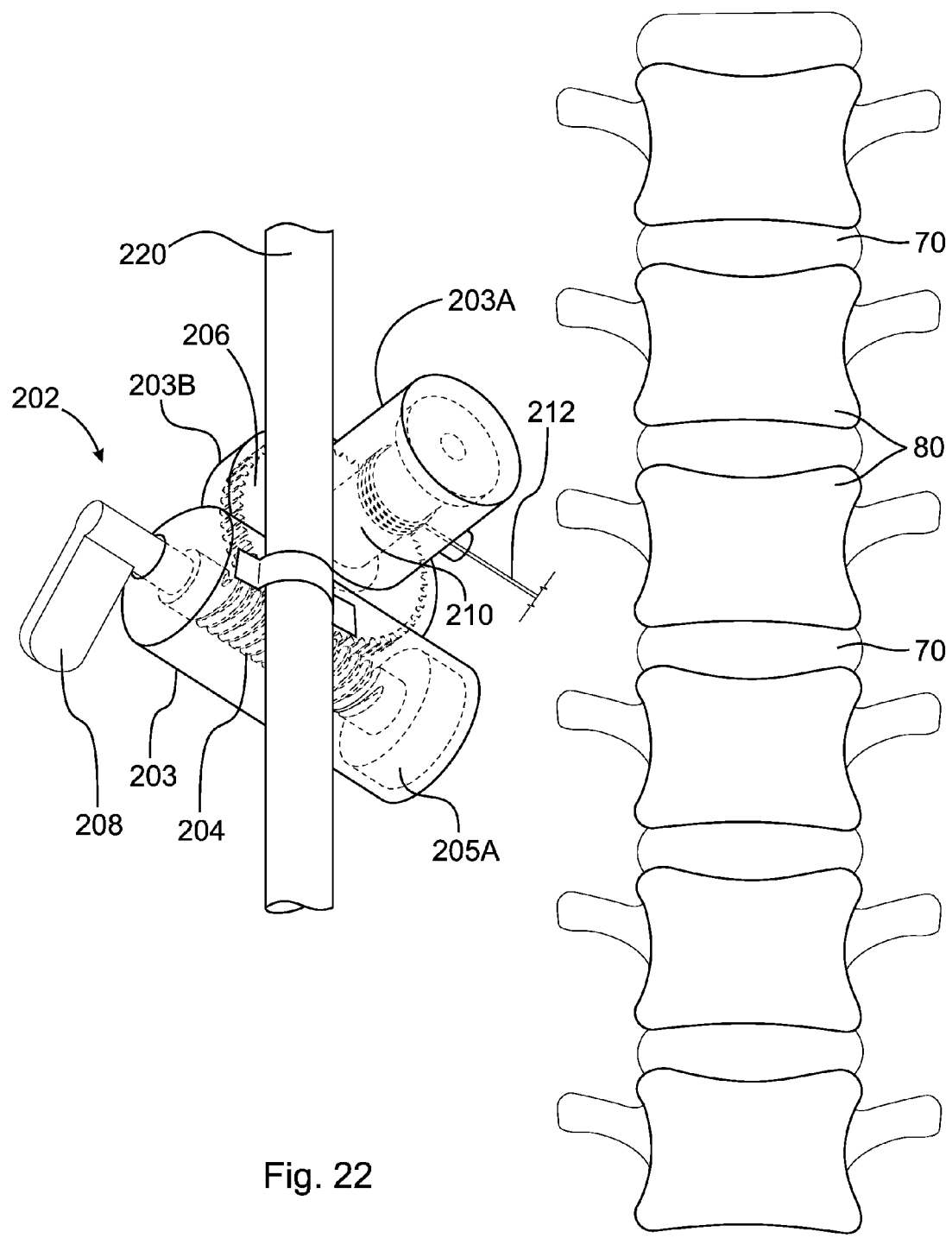
FIG. 22 is a bottom perspective view of the assembly secured to a rigid bracing rod.

FIG. 22 is a bottom perspective view of assembly 200 including rigid bracing rod 220. The components of ratcheting mechanism 202 are enclosed in housings 203, 203A, and 203B. FIG. 22 also includes a posterior schematic view of a spinal column comprising vertebrae 80 and intervertebral disks 70. Ratcheting mechanism 202 may be attached to rod 220 in different orientations relative to the spinal column. Preferably, ratcheting mechanism 202 is attached in such a way as to enable its longitudinal movement along rod 220 before it is fixed into position and to allow control lever 208 to be proximate to the external side of surrounding tissue to enable it to be operated, e.g., pressed, from outside the body of a patient. Although not shown in FIG. 22, preferably, a spring means such as those discussed above, is included in assembly 200 to ensure cable 212 is wound only a predetermined amount when lever 208 is pressed, once identified by palpation through the skin.

Figure 23:
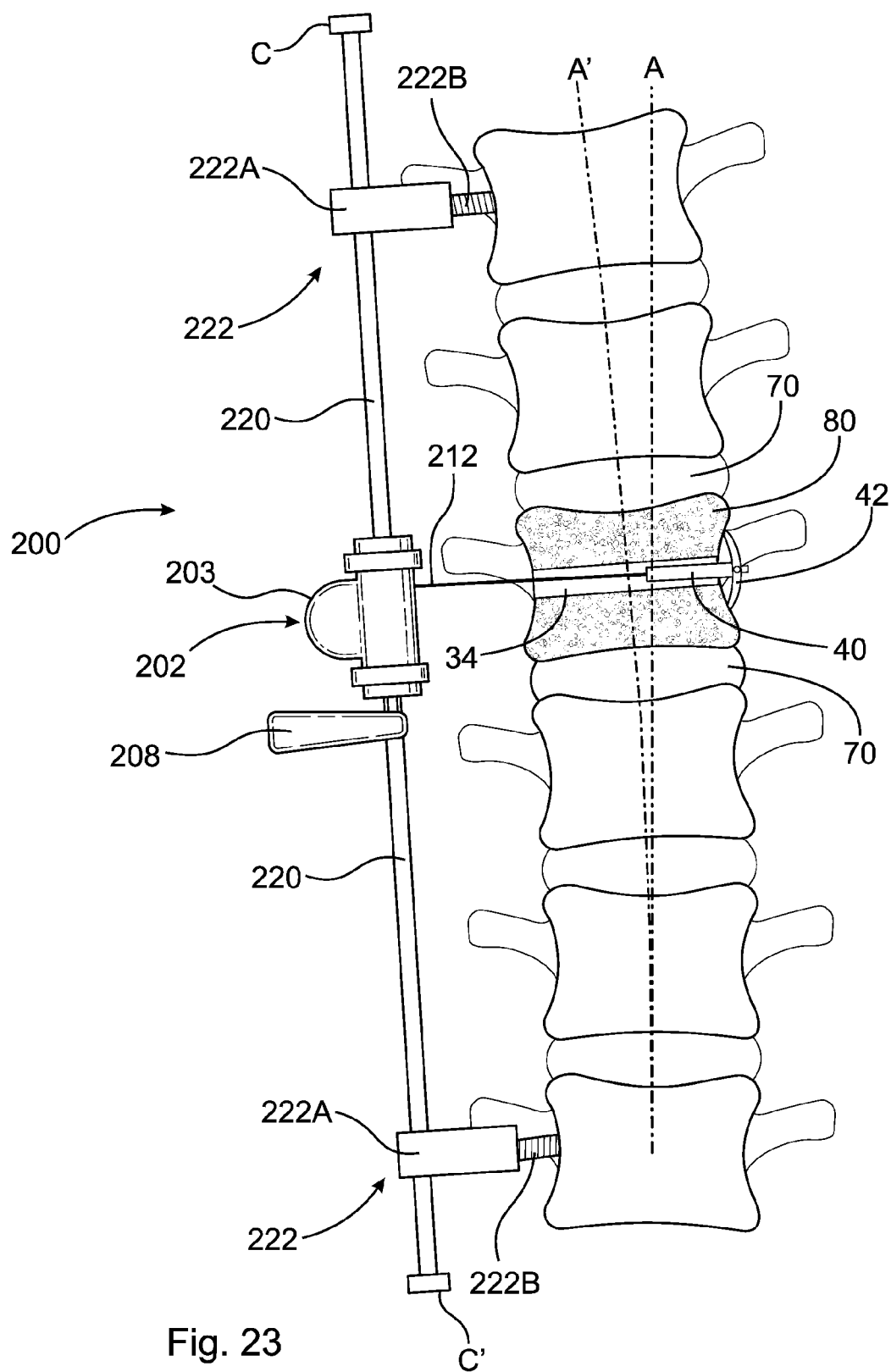
FIG. 23 is an anterior view of the assembly attached to a curved spinal column.

FIG. 23 is an anterior view of assembly 200 attached to a curved spinal column. Axis A represents the longitudinal axis of the spinal column when straightened to the ideal anatomical position, while axis A' indicates the longitudinal axis of the curved spinal column. Target vertebra 80 may be prepared to receive a vertebra fixture element, in this case toggle bolt 40, in the manner described above for example. Toggle bolt 40 extends through hole 34 such that the distal end of toggle bolt 40 extends through vertebra 80 with wings 42 extended against the side of vertebra 80. Cable 212 is attached to the proximal end of toggle bolt 40 and is retained on stem 210 of ratcheting mechanism 202. Bracing assemblies 222 are slidingly attached to bracing rod 220 above and below assembly 200 to maintain the position of assembly 200 relative to hole 34 and toggle bolt 40 so that cable 212 continues to be wound at a convenient angle, e.g., generally perpendicular to the spinal column. Bracing assemblies 222 are prevented from sliding off of bracing rod 220 via caps C and C'. It should be appreciated that additional members can be placed along bracing rod 220 to limit the movement of bracing assemblies 222 as shown in FIG. 26.

Figure 24:
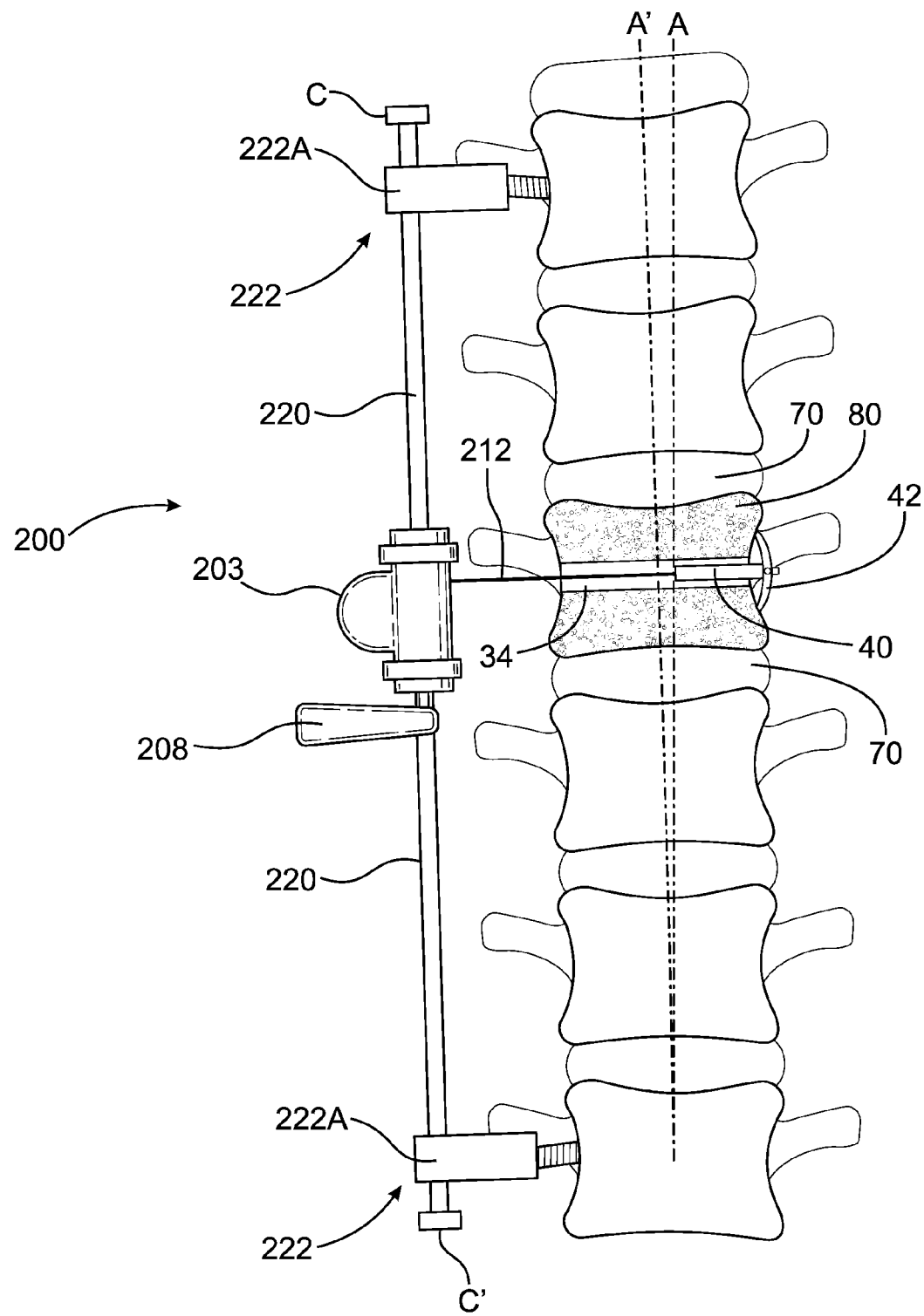
FIG. 24 is the same view as in FIG. 23 depicting the spinal column pulled straighter, i.e., closer to the desired anatomical position.
Figure 25:
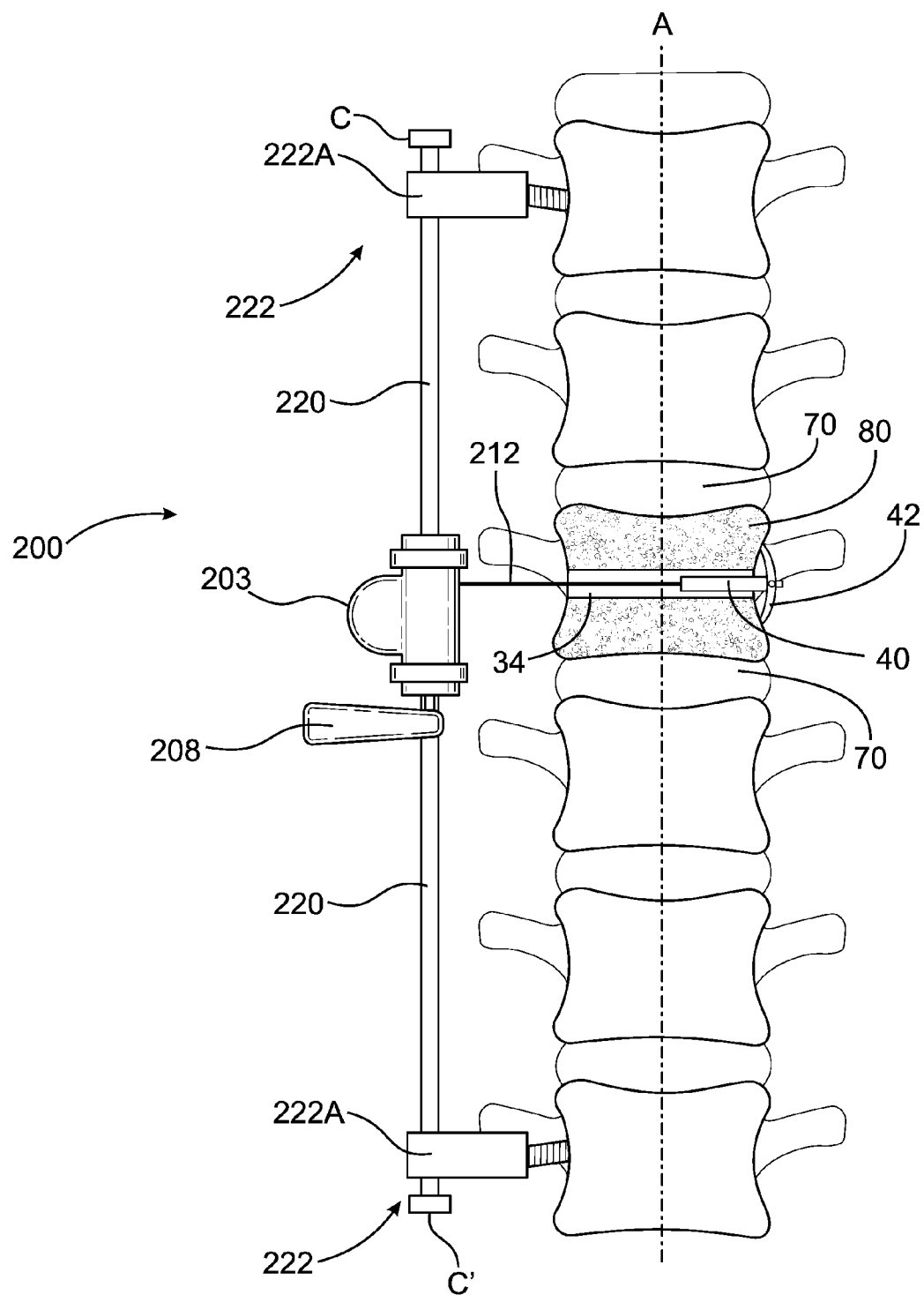
FIG. 25 shows the spinal column in the desired anatomical alignment caused by the pulling of the curve of the spine toward the bracing rod.

FIG. 24 is the same view as FIG. 23 depicting spinal column 1 pulled closer to the desired anatomical position as a result of winding cable 212 on stem 210 of ratcheting mechanism 202 (enclosed in housing 203). This is seen by the smaller diverting angle between lines A and A'. As spinal column 1 becomes straighter, it lengthens which is reflected in the decrease in the distance between each of the bracing assemblies 222 and the end of bracing rod 220 demonstrating the pivotal or sliding attachment of bracing assemblies 222 to bracing rod 220 as discussed below. FIG. 25 shows spinal column 1 in the desired anatomical alignment caused by the pulling of the curve of the spine toward bracing rod 220.

Figure 26:
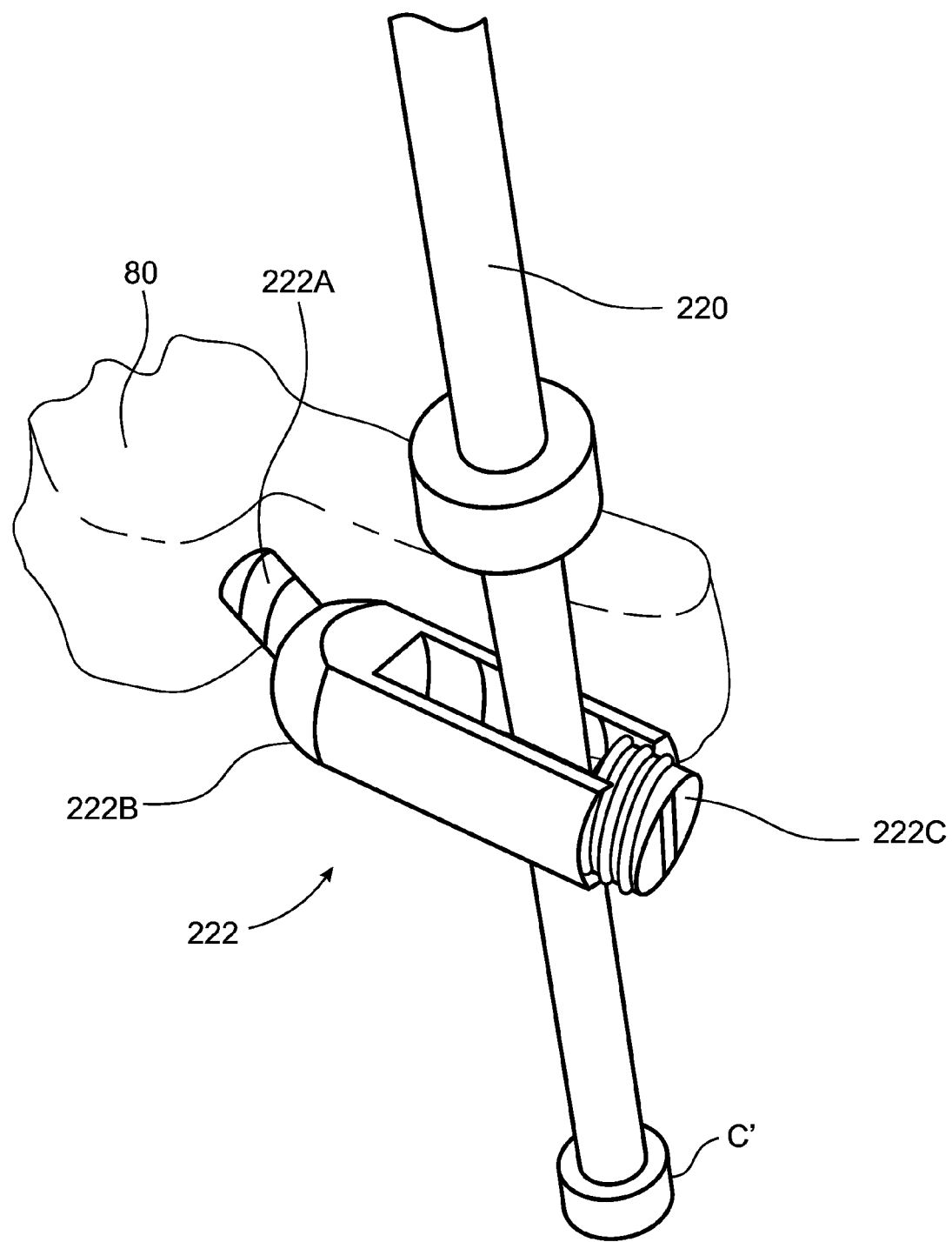
FIG. 26 is an enlarged posterior view of one embodiment of the bracing assembly used to attach the vertebra to the bracing rod.

FIG. 26 is an enlarged posterior view of one embodiment of bracing assembly 222 attached to a vertebra 80 and bracing rod 220. Screw 222A is pivotally attached to body 222B and is screwed into vertebra 80, in this case dorsal to the transverse process on the facet of the superior articular process. Holding screw 222C is threaded onto body 222B to hold bracing assembly 222 onto bracing rod 220 which passes through body 222B. The pivotal attachment of screw 222A to body 222B enables bracing assembly 222 to remain attached to vertebra 80 and to allow spinal column 1 to be pulled to a straighter alignment. Bracing assembly 222 may be attached in such a way as to enable bracing assembly 222 to slide on bracing rod 220 as spinal column 1 is straightened.

In an alternate embodiment of assembly 200, inflatable balloon anchor 214 having vanes 214B can act as the vertebra fixture element to pull spinal cord 1 into or closer to the desired alignment. As explained above and depicted in FIGS. 15A-15D regarding balloon anchor 114, balloon anchor 214 is deployed through target vertebra 80 and inflated. Balloon anchor 214 is similar to balloon anchor 114, but includes an attachment to cable 212 at its proximal end.

Figure 27:
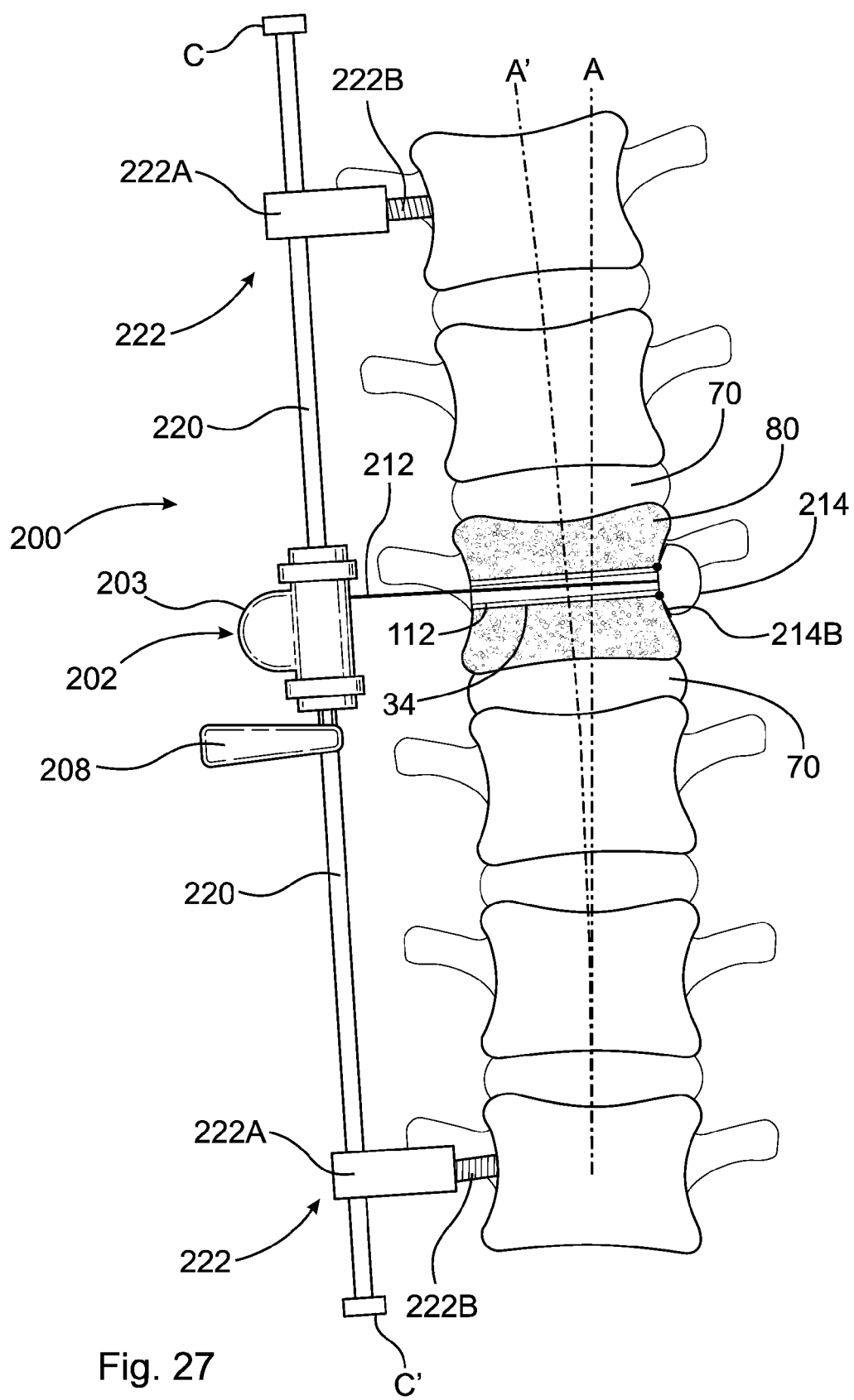
FIG. 27 depicts the second alternate embodiment of the assembly attached to a spinal cord in which an inflatable balloon anchor is extended through a target vertebra and attached to the assembly with a cable.

FIG. 27 depicts assembly 200 connected to spinal cord 1 in which balloon anchor 214 is extended through target vertebra 80 and attached to ratcheting mechanism 202 with cable 212 at its proximal end. Similar to FIG. 23, bracing assemblies 222 are pivotally attached to vertebrae of spinal column 1 and attached to bracing rod 220 above and below assembly 200 to maintain the position of assembly 200 relative to hole 34 and balloon anchor 214 so that cable 212 continues to be wound at a convenient angle, e.g., generally perpendicular to spinal column 1.

Figure 28:
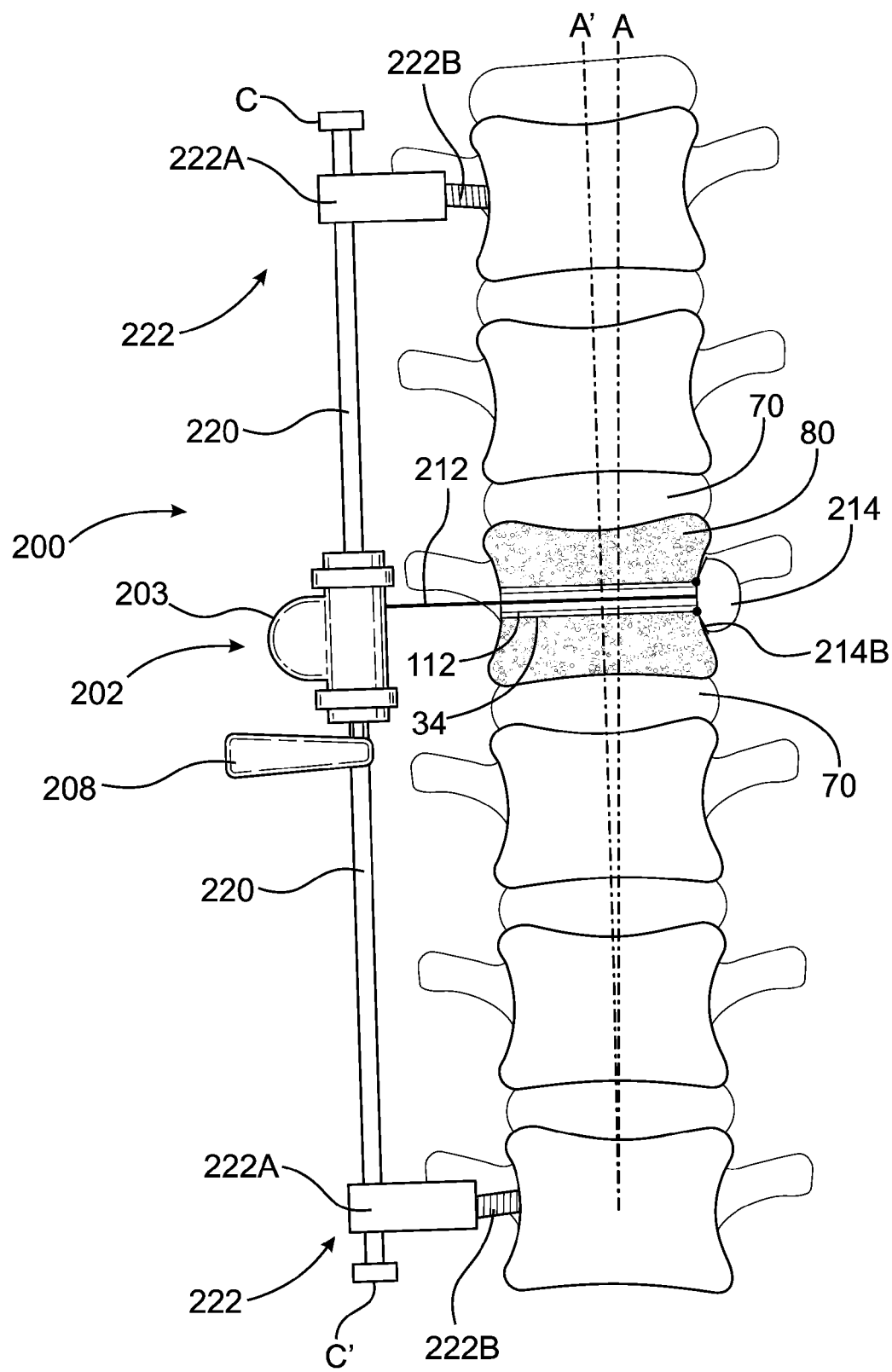
FIG. 28 is the same view as in FIG. 27 depicting the spinal column pulled straighter, i.e., closer to the desired anatomical position.
Figure 29:
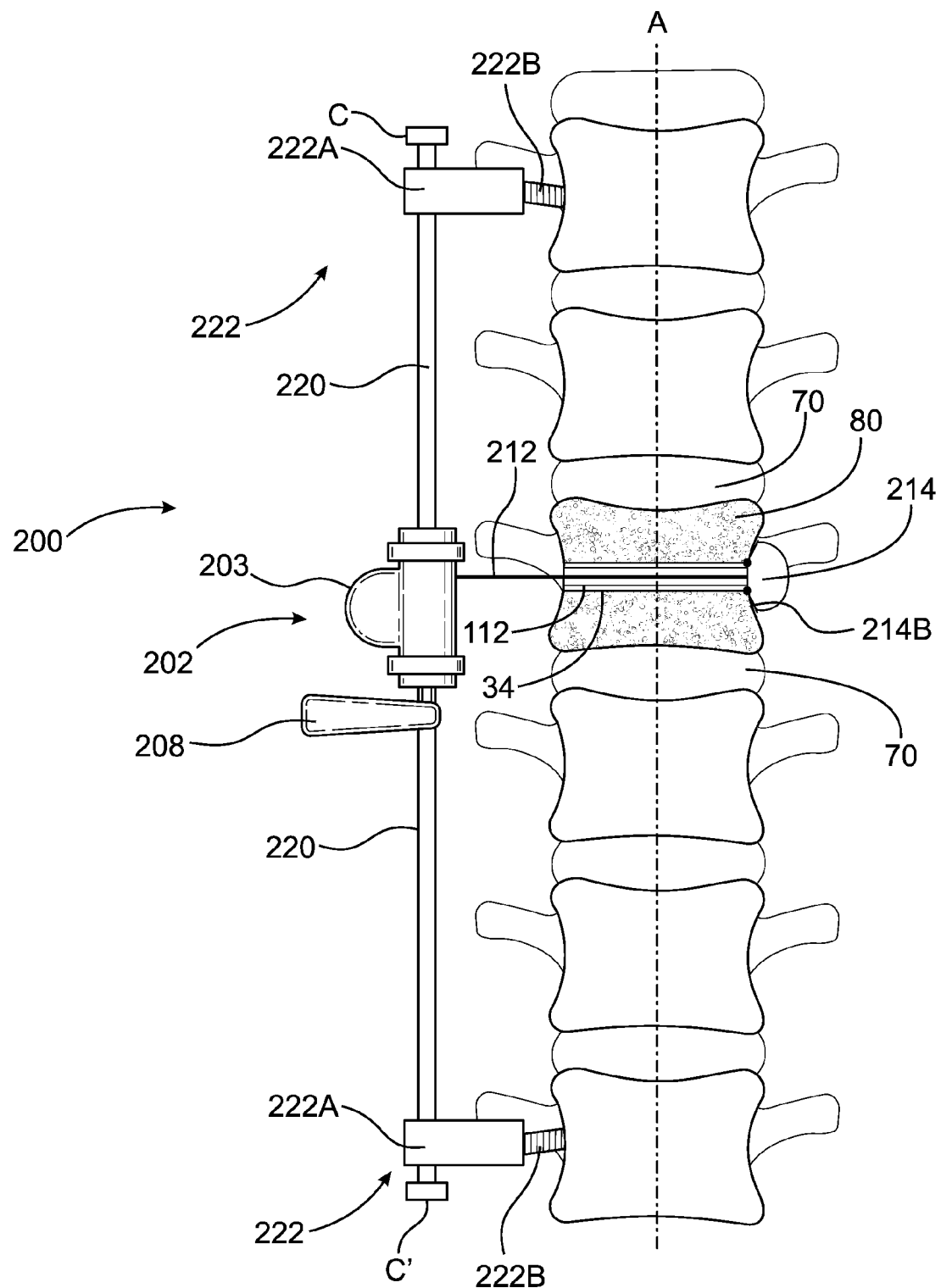
FIG. 29 is the same view as in FIG. 27 with the spinal column pulled into the desired anatomical alignment using the balloon anchor.

FIG. 28 is the same view as FIG. 27 depicting spinal column 1 pulled straighter, using balloon anchor 214 as a result of winding cable 212 on stem 210 of ratcheting mechanism 202 (enclosed in housing 203). This is seen by the smaller diverting angle between lines A and A'. As spinal column 1 becomes straighter, it lengthens which is reflected in the decrease in the distance between each of the bracing assemblies 222 and the end of bracing rod 220 demonstrating the slidable attachment of bracing assemblies 222 bracing rod 220. FIG. 29 shows spinal column 1 in the desired anatomical alignment caused by the pulling of the curve of the spine toward bracing rod 220.

Figure 30:
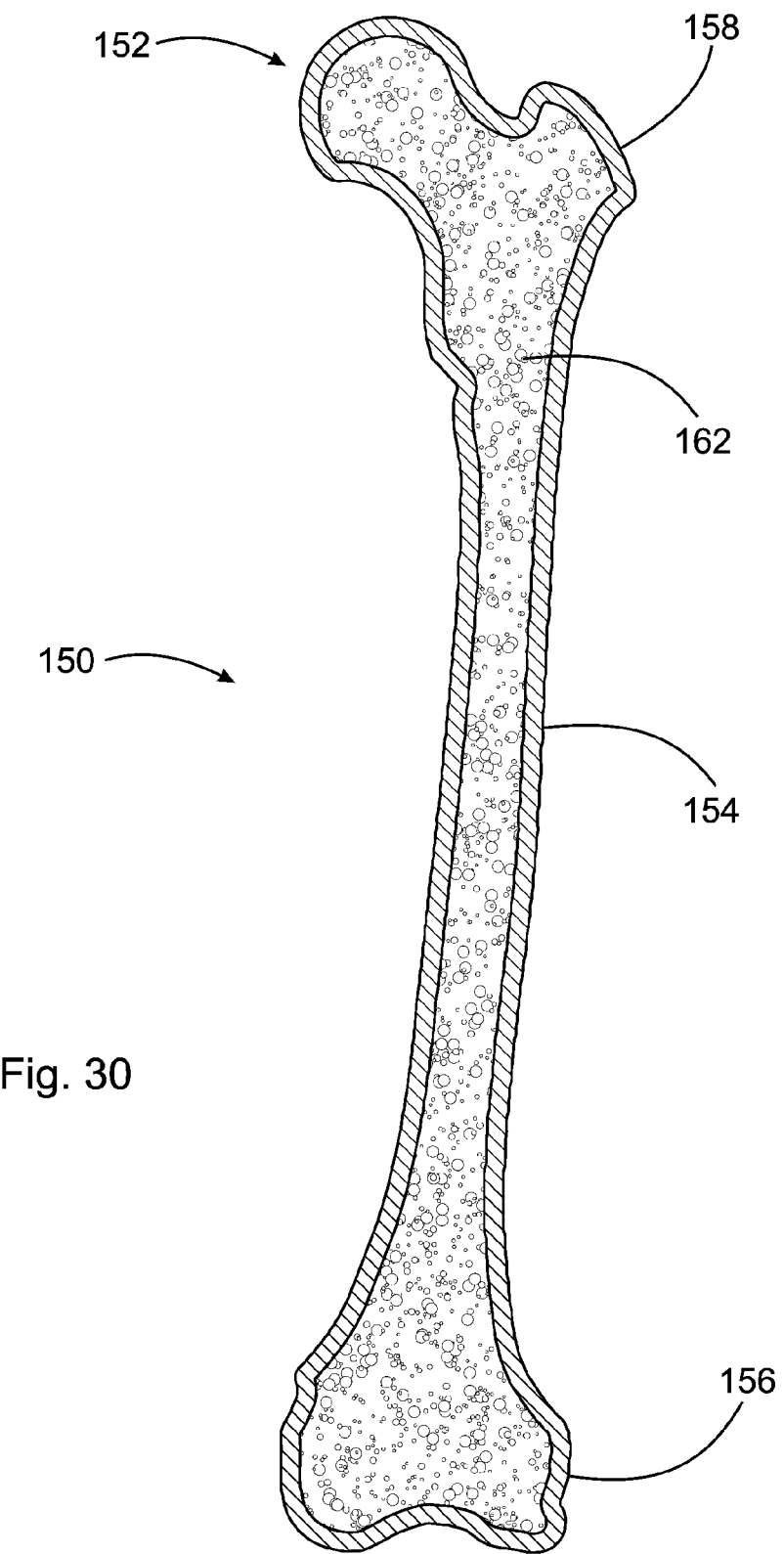
FIG. 30 is a longitudinal cross-sectional view of a femur.
Figure 31:
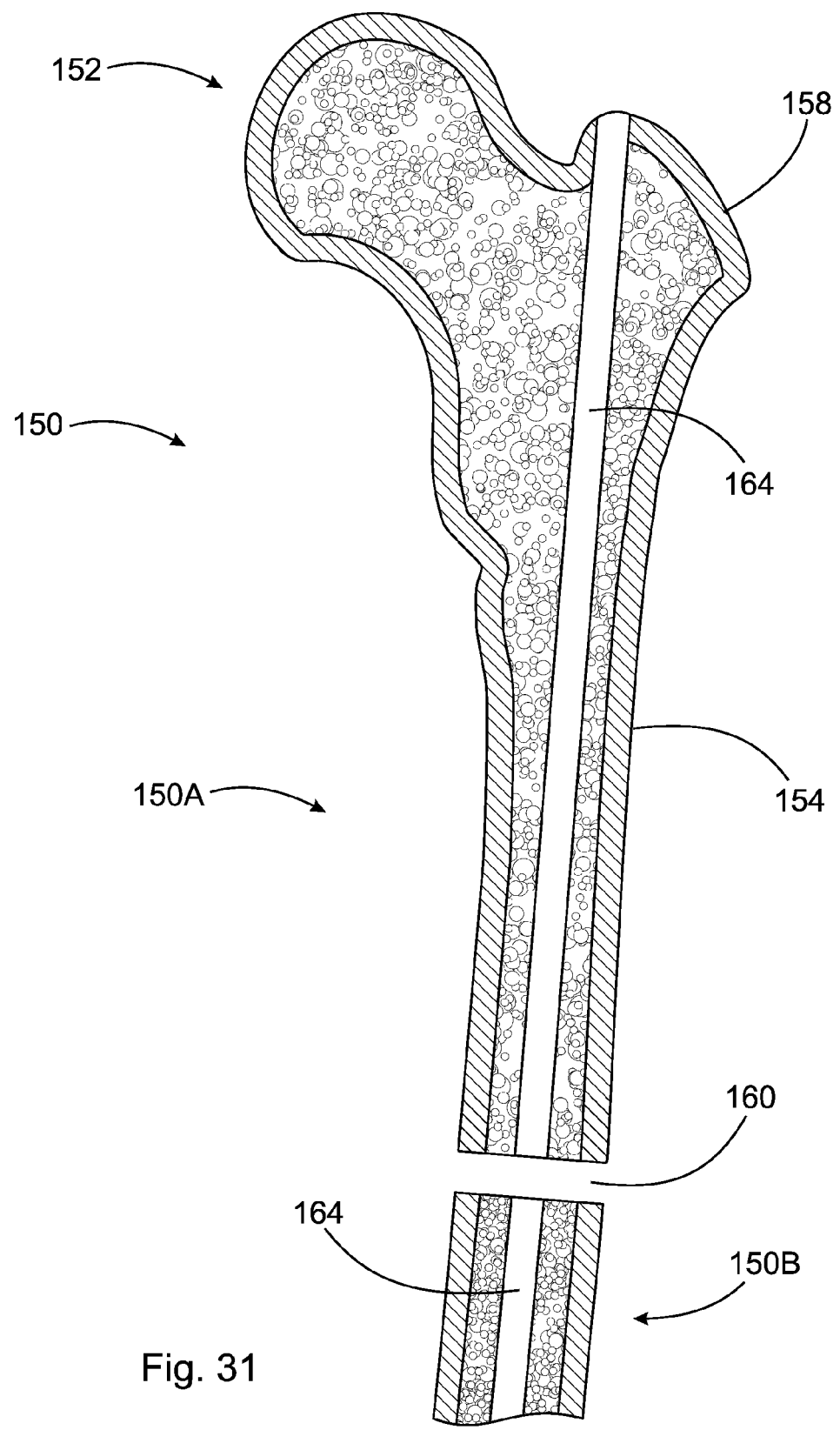
FIG. 31 is an enlarged cross-sectional view of a femur showing an osteotomy separating the femur into an upper section and a lower section.

FIG. 30 is a longitudinal cross-sectional view of femur 150 including upper extremity 152, shaft or body 154, lower extremity 156, and greater trochanter 158. Also seen is bone marrow 162. FIG. 31 is an enlarged cross-sectional view of femur 150 showing osteotomy or gap 160 separating femur 150 into upper and lower sections. Passage 164 is created by an intramedullary nail by inserting the nail into a hole drilled through greater trochanter 158 or other region of upper extremity 152 in a controlled manner. An example of a suitable intramedullary nail is supplied by Ellipse Technologies in Aliso Viego, Calif. under its Precice® product line.

Figure 32A:
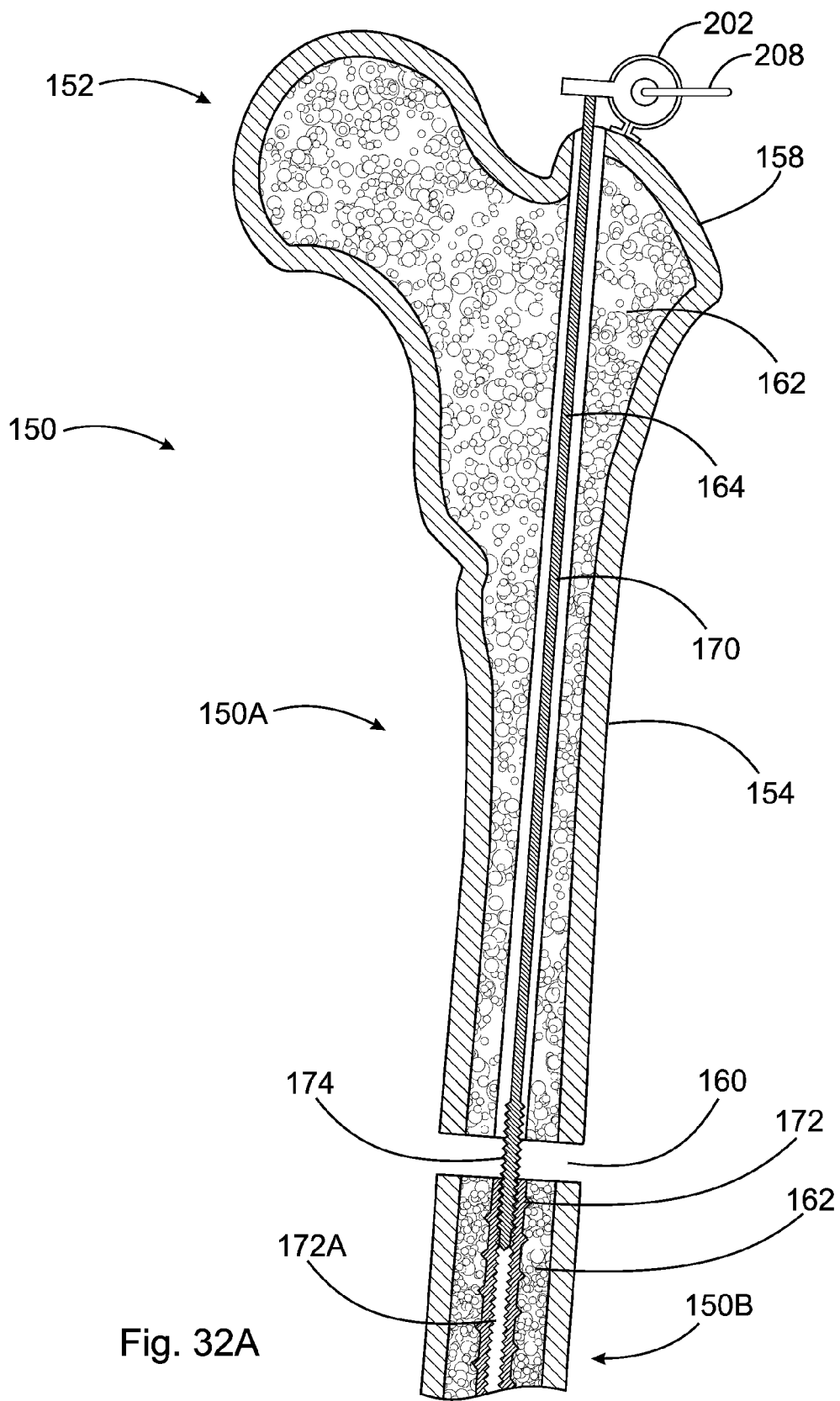
FIG. 32A is the same longitudinal cross-sectional view of the femur as shown in FIG. 31 including a bone lengthening assembly including a worm gear.
Figure 32B:
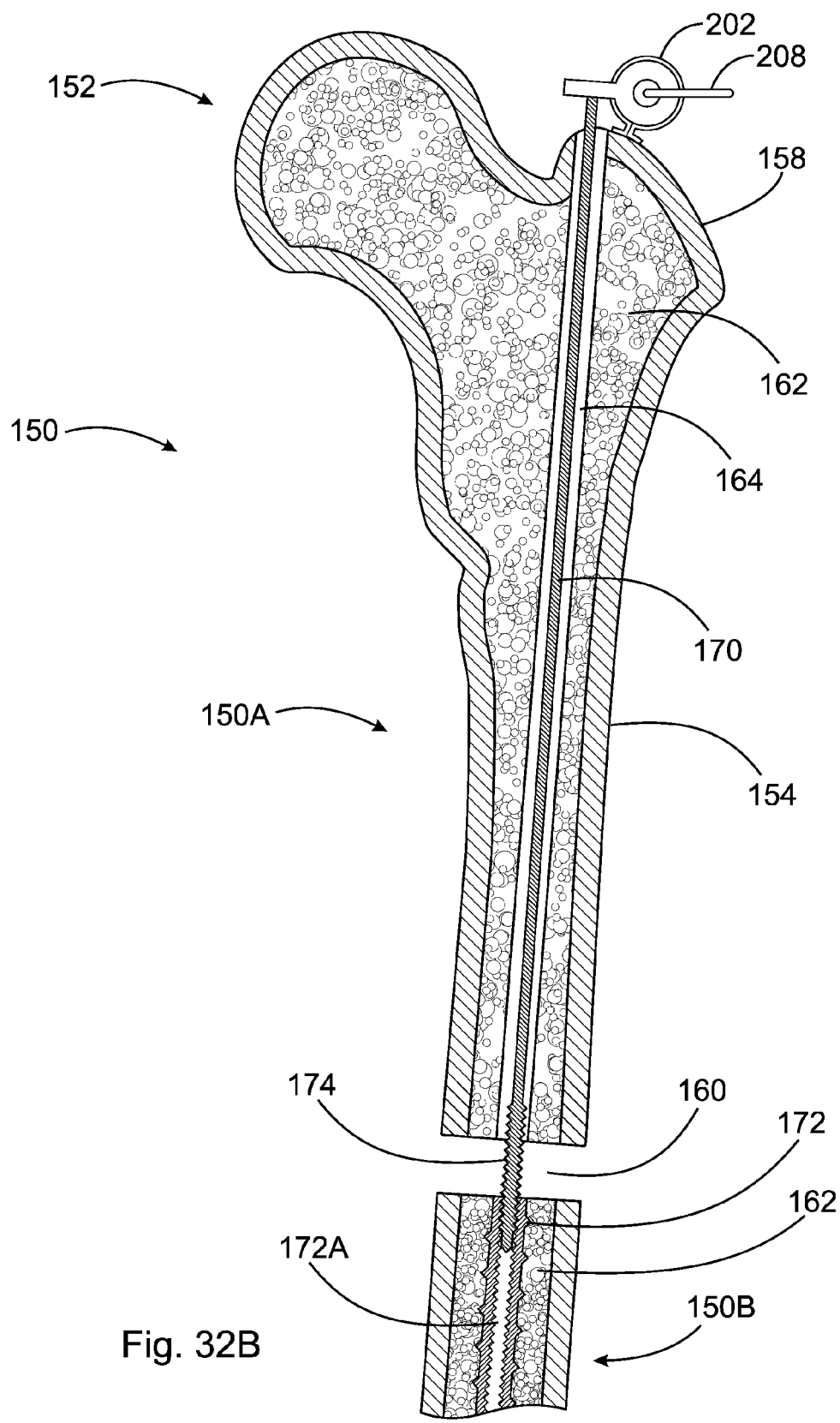
FIG. 32B is a view similar to that of FIG. 32A wherein the gap formed by the osteotomy is widened after the separation rod is turned.

FIG. 32A is the same longitudinal cross-sectional view of femur 150 depicting a novel bone lengthening assembly that includes ratcheting mechanism 202. Screw shell 172 is placed in the distal section 150B of femur 150 below osteotomy 160 to act as an embodiment of a distal base portion of the assembly. This placement may be effected by the intramedullary nail when it is passed into distal section 150B. Like outer screw shell 22 discussed above, screw shell 172 includes inner threads 172A. Separation rod 170 ("rod 170") is an upper proximal adjustable portion of the assembly and includes threaded end 174 ("end 174") at its distal end. Separation rod 170 is operatively attached to ratcheting mechanism 202. End 174 extends through osteotomy 160 and is inserted into screw shell 172 so the threads of end 174 threadably interact with inner threads 172A. When control lever 208 on ratcheting mechanism 202 is activated, separation rod 170 rotates to turn threaded end 174 into shell 172 thereby pushing distal section 150B of bone 150 away from upper section 150A widening gap 160. This is depicted in FIG. 32B in which the gap formed by osteotomy 160 is widened after separation rod 170 is turned. In a typical embodiment, ratcheting mechanism 202 is configured to turn rod 170 to widen the gap 1 mm with each movement of control lever 208. Although not seen, it is understood that ratcheting mechanism 202 includes a spring means such as coil spring 211 with rebound board 208A and/or torsion spring 205A discussed above or other spring devices to return control lever 208 to a starting position.

Figure 33:
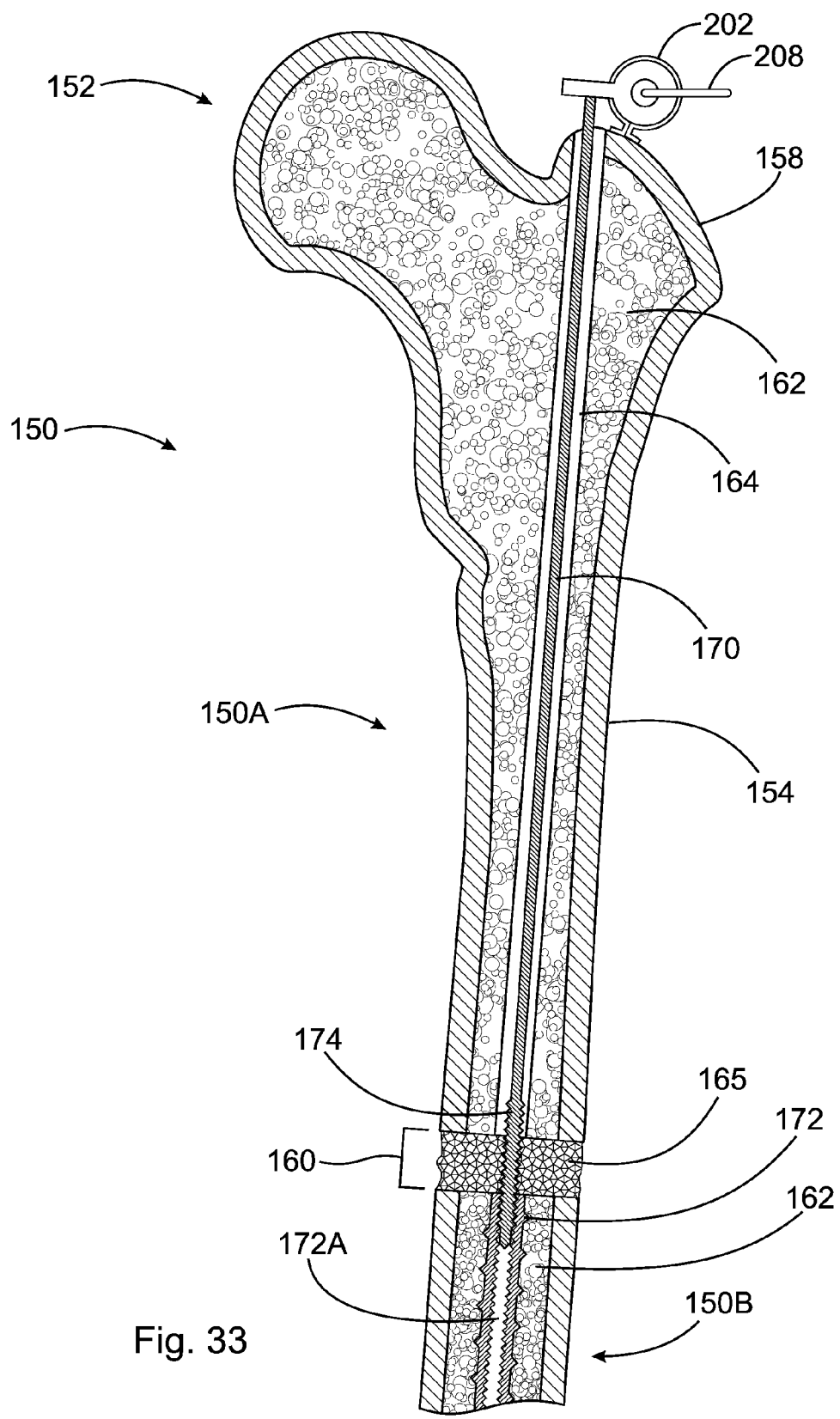
FIG. 33 shows bone growth that naturally occurs filling the gap created by the osteotomy.
Figure 34:
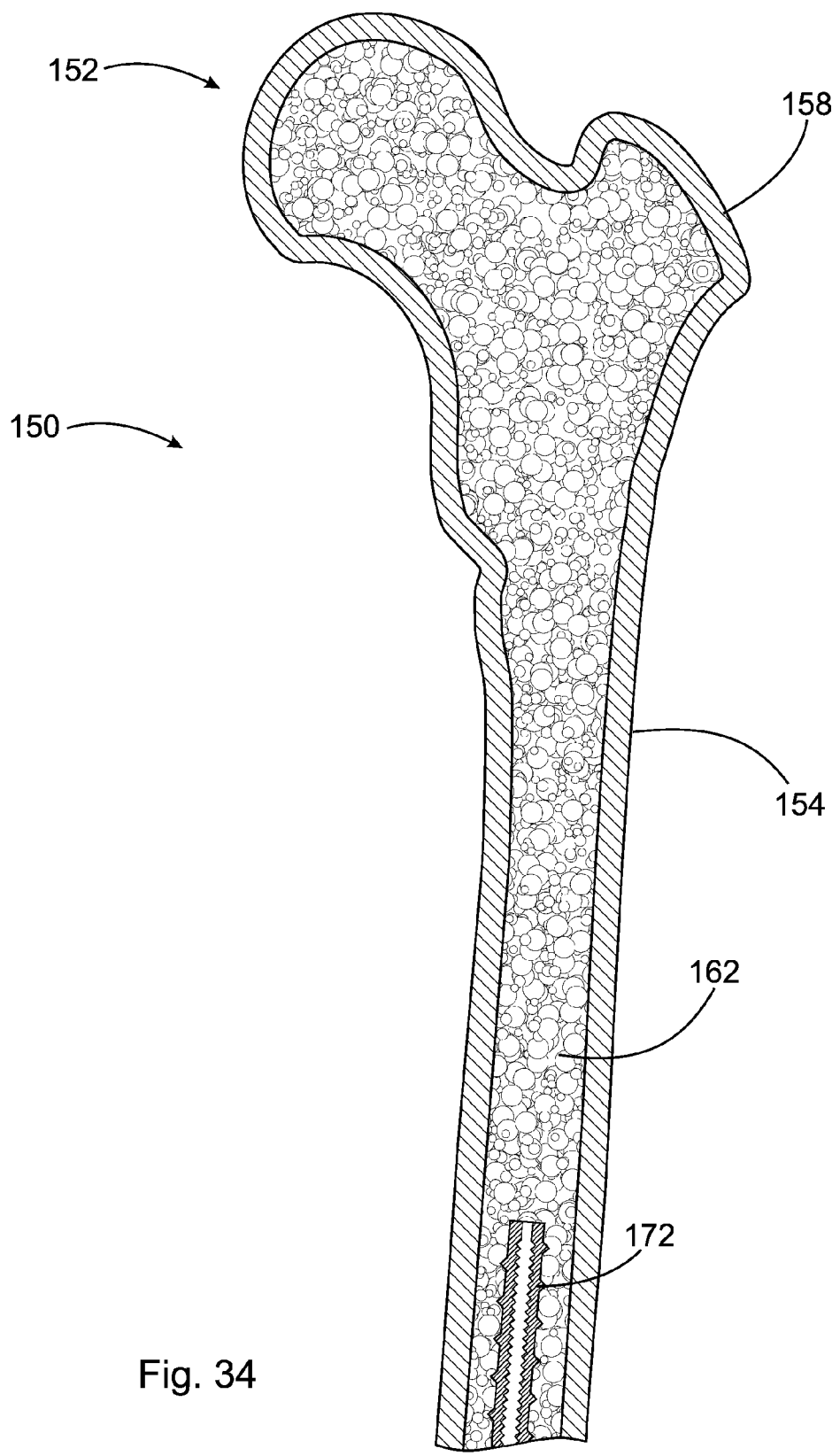
FIG. 34 depicts the completion of the bone growth after the removal of the separation rod and worm gear; and, FIG. 35 is the same view as in FIG. 32 showing the use of an electric motor to turn the separation rod.

FIG. 33 shows bone growth 165 that naturally occurs to fill the gap created by osteotomy 160. As can be seen, separation rod 170, which may include threaded end 174, spans osteotomy 160 to continue widening gap 160 to a desired width showing that new bone growth occurs while the separation procedure continues. In other words, the bone growth continues as gap 160 is widened to the desired width. Ultimately, as seen in FIG. 34, when gap 160 is widened to the target width, separation rod 170 and ratcheting mechanism 202 are withdrawn and bone and marrow growth continues to completely fill in gap 160 until the bone density is the same or almost the same as the rest of femur 150. It is noted that screw shell 172 remains in femur 150. FIG. 34 also shows bone marrow 162 having filled in passage 164 with femur 150 lengthened by the width of the gap that was lengthened by ratcheting mechanism 202.

In the embodiment of the bone lengthening assembly discussed above, similar to assembly 200 discussed above, worm screw 204 is rotated a specific number of degrees in order to rotate separation rod 170 to produce a predetermined distance, e.g., 1 mm. between proximal section 150A and distal section 150B of femur 150. After an established amount of time, ratcheting mechanism 202 is again rotated to separate the two femur sections another 1 mm. As with ratcheting mechanism 202 in the spinal alignment assembly 200 discussed above, control lever 208 is pressed to turn worm screw 204 to rotate separation rod 170 to enable the additional 1 mm separation. Preferably, assembly 200 is configured such that lever 208 only rotates rod 170 enough to widen gap 160 a predetermined distance, e.g., 1 mm, when lever 208 is pressed or activated. It is recognized by persons having skill in the art that ratcheting mechanism 202 may be mounted on greater trochanter 158 or another feature close to the external surface of the surrounding tissue to provide easy access to lever 208 by palpation through the skin.

Figure 35:
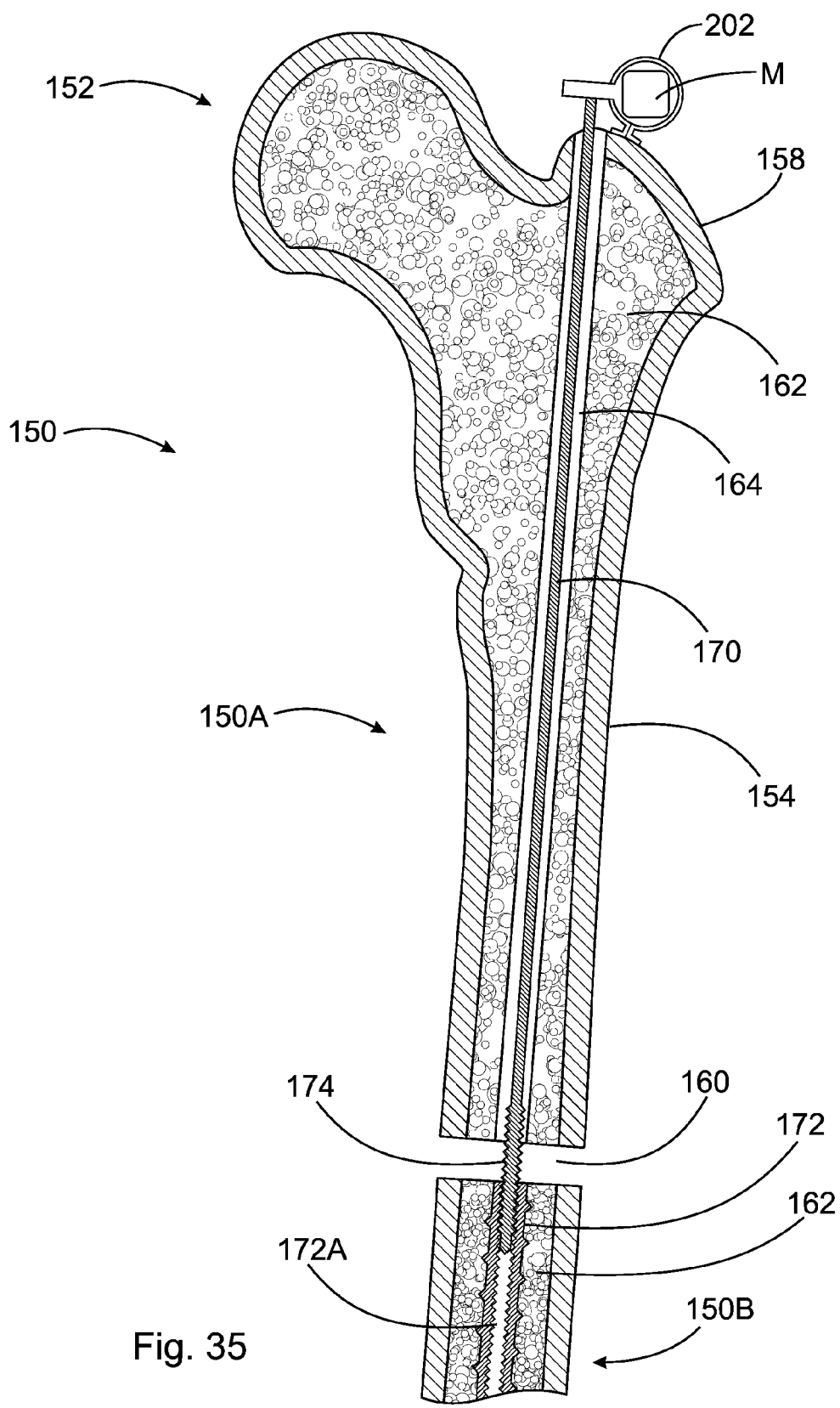

In an alternate embodiment, shown in FIG. 35, control lever 208 is replaced by motor M having a Bluetooth® receiver capability. A Bluetooth® transmitter may be used to transmit a programmed command to motor M to turn worm gear 204 the predetermined amount to rotate separation rod 170. A similar motor with Bluetooth® receiver capability may be used to turn worm gear 200 when used in spine straightening assembly 200.

The use of a worm gear in a bone lengthening assembly provides the advantage of precision in widening the gap between the divided portions of the bone by the same distance each time the rod is rotated by ratcheting mechanism 202. In addition, the ratchet mechanism described above with respect to the spinal alignment assembly 200, may be used in the bone lengthening assembly to hold the worm gear in position to prevent possibly slippage of worm screw 204 ensuring the gap continues to be widened to the desired width without the upper section 150A falling back toward the lower section 150B of the femur 150. Persons having ordinary skill in the art recognize that the other bones, such as the humerus or tibia may be targeted in a bone lengthening process, and such rod lengthening can be used to stretch a curved spine if the distal ends of the rod are secured to the spine with pedicle screws.

Thus, it is seen that the objects of the invention are efficiently obtained, although changes and modifications to the invention should be readily apparent to those having ordinary skill in the art, which changes would not depart from the spirit and scope of the invention as claimed.

REFERENCE NUMBERS

P Person
1 Spinal column
2 Upper curve
3 Lower curve
4 Brace
5 Brace
20 Bone screw
22 Outer screw shell
22A Threads
22B Internal threads
24 Inner screw
24A Threads
24B Cap
25 Distal end point
26 Lumen
30 Rod
30A End
32 Receiver
34 Screw hole
34A Axis
36 Aperture
36A Wall
37 Set screw
37A Threaded through-bore for set screw
38 Annular lip
40 Toggle bolt
41 Shaft
42 Deployable wings
44 Pivot attachment
46 Cable
50 Tube
50A Tube aperture
52 Lip
52A Threads
54 Set screw
60 Pulling tool
70 Vertebral disc
80 Vertebra
100 Assembly
102 Needle
102A Stylet
110 Bone anchor
112 Tube 114 Balloon
114A Anchor tip
114B Array
116 Proximal end
117 Distal end
118 Fluid conduit
118A Port
118B Port
120 Bone screw
122 Strut
130 Bone screw-strut-construction
150 Femur
150A Upper section
150B Lower section
152 Upper extremity
154 Body
156 Lower extremity
158 Greater trochanter
160 Gap
162 Bone marrow
164 Passage
165 Bone growth
170 Separation rod
172 Screw shell
172A Inner threads
174 Threaded end
200 Assembly
202 Ratcheting mechanism
203 Housing
203A Housing
203B Housing
204 Worm screw
205A Torsion spring
205B Coil spring
206 Worm wheel
208 Control lever
208A Rebound board
210 Stem
212 Cable
216 Assembly
216A Ratchet gear
216B Ratchet gear
217 Spring
220 Bracing rod
222 Bracing assembly
222A Screw
222B Body
222C Holding screw
M Motor
BA Back
B Brace
B' Brace
A Axis
C Cap
C' Cap

What is claimed is:

1. A subcutaneous implantable device for aligning a spine having a plurality of vertebrae, comprising:
   a first brace assembly arranged to be secured to a first vertebra of said spine;
   a second brace assembly arranged to be secured to a second vertebra of said spine;
   a rod secured by said first and second brace assemblies, said rod arranged for limited sliding movement within said first and second brace assemblies;
   a cable arranged to be secured to a third vertebra of said spine, wherein:
      said third vertebra is located between said first and second vertebrae; and,
      said cable is arranged for pulling said third vertebra towards said rod; and,
   a gear mechanism attached to said rod, including:
      a stem arranged to wind said cable;
      a wheel connected to said stem, wherein said wheel includes gear teeth;
      a screw operatively arranged to rotate said gear teeth of said wheel in a single direction; and,
      a control lever attached to rotate said screw in a single direction.

2. The implantable device recited in claim 1, wherein said cable is secured to said third vertebra with an anchor.

3. The implantable device recited in claim 2, wherein said anchor is a molly bolt.

4. The implantable device recited in claim 2, wherein said anchor is a toggle bolt.

5. The implantable device recited in claim 2, wherein said anchor is a balloon.

6. The implantable device recited in claim 5, wherein said balloon is inflated within said third vertebra.

7. The implantable device recited in claim 1, wherein said control lever is connected to a fixed surface by a resilient member and said control lever is rotatable only to a limited extent.

8. The implantable device recited in claim 1, wherein said control lever is connected to a resilient member to urge said control lever to a starting position after said control lever is pressed.

9. The implantable device recited in claim 1, wherein said control lever is connected to a first gear which engages a second gear to rotate said second gear in said single direction.

10. The implantable device recited in claim 1, wherein said control lever is connected to a first gear having gear teeth and said gear mechanism includes a pawl arranged to engage said gear teeth of said first gear to enable said first gear to rotate in said single direction.

11. The implantable device recited in claim 1, wherein said first and second bracing assemblies are pivotable relative to said rod.

12. The implantable device recited in claim 1, wherein said control lever is arranged to be palpated subcutaneously.

13. The implantable device recited in claim 1, wherein the gear mechanism includes a worm gear.

14. A subcutaneous implantable device for aligning a spine having a plurality of vertebrae, comprising:
   a first brace assembly arranged to be secured to a first vertebra of said spine;
   a second brace assembly arranged to be secured to a second vertebra of said spine;
   a rod secured by said first and second brace assemblies, said rod arranged for limited sliding movement within said first and second brace assemblies;
   a gear mechanism attached to said rod;
   a control means attached to said gear mechanism;
   a cable arranged to be secured to a third vertebra of said spine with a balloon anchor, wherein said third vertebra is located between said first and second vertebrae, and wherein said cable is arranged for pulling said third vertebra towards said rod.

15. The implantable device recited in claim 14, wherein said gear mechanism includes a stem arranged to wind said cable.

16. The implantable device recited in claim 15, wherein said gear mechanism includes a wheel connected to said stem, wherein said wheel includes gear teeth.

17. The implantable device recited in claim 16, wherein said gear mechanism includes a screw operatively arranged to rotate said gear teeth of said wheel in a single direction.

18. The implantable device recited in claim 17, wherein said gear mechanism includes a control lever attached to said screw to rotate said screw in said single direction.

19. The implantable device recited in claim 18, wherein said control lever is connected to a fixed surface by a resilient member and said control lever is rotatable only to a limited extent.

20. The implantable device recited in claim 18, wherein said control lever is connected to a resilient member to urge said control lever to a starting position after said control lever is pressed.

21. The implantable device recited in claim 18, wherein said control lever is connected to a first gear which engages a second gear to rotate said second gear in said single direction.

22. The implantable device recited in claim 18, wherein said control lever is connected to a first gear having gear teeth and said gear mechanism includes a pawl arranged to engage said gear teeth of said first gear to enable said first gear to rotate in said single direction.

\* \* \* \* \*